(12) United States Patent
Rogers et al.

(10) Patent No.: US 8,450,381 B2
(45) Date of Patent: May 28, 2013

(54) MICROCHANNEL COMPRESSION REACTOR

(75) Inventors: William Allen Rogers, Marysville, OH (US); Paul William Neagle, Plain City, OH (US); Michael Alan Marchiando, Plain City, OH (US); Christopher Paul Well, Pickerington, OH (US); Robert Dwayne Litt, Westerville, OH (US); Ronald Chester Pasadyn, Missouri City, TX (US); G. Bradley Smith, Rock Hill, SC (US); Charles Robert Miele, Columbus, OH (US); Thomas Peter Forte, Columbus, OH (US); Jimmy Glen Pelham, Bartlesville, OK (US)

(73) Assignee: Velocys, Inc., Plain City, OH (US)

( * ) Notice: Subject to any disclaimer, the term of this patent is extended or adjusted under 35 U.S.C. 154(b) by 0 days.

(21) Appl. No.: 13/427,647

(22) Filed: Mar. 22, 2012

(65) Prior Publication Data

US 2012/0184633 A1    Jul. 19, 2012

Related U.S. Application Data

(63) Continuation of application No. 12/870,064, filed on Aug. 27, 2010, now abandoned, which is a continuation of application No. 12/386,256, filed on Apr. 15, 2009, now Pat. No. 7,807,113, which is a continuation of application No. 11/052,455, filed on Feb. 7, 2005, now Pat. No. 7,569,195, which is a continuation-in-part of application No. 10/774,298, filed on Feb. 6, 2004, now abandoned.

(51) Int. Cl.
| | |
|---|---|
| *C07C 27/00* | (2006.01) |
| *C07C 27/06* | (2006.01) |
| *B01J 10/00* | (2006.01) |
| *B01J 19/00* | (2006.01) |
| *B01J 8/00* | (2006.01) |
| *B01J 8/04* | (2006.01) |
| *B01J 8/02* | (2006.01) |
| *B01J 35/02* | (2006.01) |

(52) U.S. Cl.
USPC ........... 518/728; 518/702; 518/703; 518/706; 518/707; 518/712; 518/713; 518/714; 518/715; 422/129; 422/130; 422/600; 422/630; 422/198; 422/211

(58) Field of Classification Search
USPC .. 422/129, 130, 198, 211, 600, 603; 518/702, 518/703, 706, 707, 712–715
See application file for complete search history.

(56) References Cited

U.S. PATENT DOCUMENTS 2,462,517 A    2/1949  Leverenz
(Continued)

FOREIGN PATENT DOCUMENTS

CA         2220901        11/1996
(Continued)

OTHER PUBLICATIONS

Freemantle, Michael, Microprocessing on a Large Scale, Chemical & Engineering News, Oct. 11, 2004, copyright 2004, pp. 39-43, vol. 82, No. 41, American Chemical Society, USA.
(Continued)

*Primary Examiner* — Jill Warden
*Assistant Examiner* — Natasha Young
(74) *Attorney, Agent, or Firm* — Taft Stettinius & Hollister LLP

(57) ABSTRACT

The present invention includes a removable microchannel unit including an inlet orifice and an outlet orifice in fluid communication with a plurality of microchannels distributed throughout the removable microchannel unit, and a pressurized vessel adapted have the removable microchannel unit mounted thereto, the pressurized vessel adapted to contain a pressurized fluid exerting a positive gauge pressure upon at least a portion of the exterior of the removable microchannel unit. The invention also includes a microchannel unit assembly comprising a microchannel unit operation carried out within a pressurized vessel, where pressurized vessel includes a pressurized fluid exerting a positive gauge pressure upon an exterior of the microchannel unit operation, and where the microchannel unit operation includes an outlet orifice in fluid communication with an interior of the pressurized vessel.

8 Claims, 20 Drawing Sheets

U.S. PATENT DOCUMENTS

| | | | |
|---|---|---|---|
| 2,997,435 A | 8/1961 | Millar et al. | |
| 3,515,520 A | 6/1970 | Hervert | |
| 4,167,915 A | 9/1979 | Toole et al. | |
| 4,670,404 A | 6/1987 | Swift et al. | |
| 5,167,930 A | 12/1992 | Fassbender | |
| 5,811,062 A | 9/1998 | Wegeng et al. | |
| 5,932,182 A | 8/1999 | Blaney | |
| 6,126,723 A | 10/2000 | Drost et al. | |
| 6,159,434 A | 12/2000 | Gonjo et al. | |
| 6,190,624 B1 | 2/2001 | Romatier | |
| 6,192,596 B1 | 2/2001 | Bennett et al. | |
| 6,200,536 B1 | 3/2001 | Tonkovich et al. | |
| 6,558,634 B1 * | 5/2003 | Wang et al. | 422/173 |
| 6,797,243 B2 * | 9/2004 | Arcuri et al. | 422/211 |
| 6,827,095 B2 * | 12/2004 | O'Connor et al. | 137/15.01 |
| 7,118,917 B2 | 10/2006 | Bergh et al. | |
| 7,172,735 B1 | 2/2007 | Lowe et al. | |
| 7,234,514 B2 | 6/2007 | Vogel | |
| 7,569,195 B2 | 8/2009 | Rogers et al. | |
| 7,807,113 B2 | 10/2010 | Rogers et al. | |
| 2002/0028164 A1 | 3/2002 | Schutte et al. | |
| 2002/0182735 A1 | 12/2002 | Kibby et al. | |
| 2004/0081600 A1 | 4/2004 | Moreno et al. | |
| 2005/0025677 A1 | 2/2005 | Oberbeck et al. | |

FOREIGN PATENT DOCUMENTS

| | | |
|---|---|---|
| DE | 200 18 916 U1 | 3/2002 |
| EP | 1 400 280 A1 | 3/2004 |
| EP | 05 71 3077 | 3/2013 |
| GB | 2 128 013 A | 4/1984 |
| WO | WO 01/41916 A1 * | 6/2001 |
| WO | WO 2005/077516 A1 | 8/2005 |

OTHER PUBLICATIONS

Thayer, Ann M., Harnessing Microreactions, Chemical & Engineering News, May 30, 2005, copyright 2005, pp. 43-52, vol. 83., No. 22, American Chemical Society USA.

Wang, et al., Intensification of Gas-To-Liquid (GTL) Process Using Microchannel Technology, May 5, 2003, Pacific Northwest National Laboratory, Richland, WA and Velocys, Inc., Columbus, Ohio, USA.

Driscol, et al., 300 MWe Supercritical CO2 Plant Layout and Design, Topical Report, Report No. MIT-GFR-014, Jun. 2004, Center for Advanced Nuclear Energy Systems, MIT Nuclear Engineering Department, Cambridge, MA., USA.

Levent et al., "Production of hydrogen-rich gases from steam reforming of methane in an automatic catalytic microreactor", International Journal of Hydrogen Energy 28, (2003) pp. 945-959, © 2003, Published by Elsevier Science Ltd.

* cited by examiner

US 8,450,381 B2

MICROCHANNEL COMPRESSION REACTOR

CROSS REFERENCE TO RELATED APPLICATIONS

This application is a continuation of application Ser. No. 12/870,064, filed Aug. 27, 2010, now abandoned, which was a continuation of application Ser. No. 12/386,256, filed Apr. 15, 2009, now U.S. Pat. No. 7,807,113, which was a continuation of application Ser. No. 11/052,455, filed Feb. 7, 2005, now U.S. Pat. No. 7,569,195 which is a continuation-in-part of application Ser. No. 10/774,298, filed Feb. 6, 2004, now abandoned, the disclosures of which are incorporated herein by reference.

BACKGROUND

1. Field of the Invention

The present invention is directed to chemical processing unit operations and, more specifically, to microchannel-based chemical processing unit operations.

2. Background of the Invention

The present disclosure is related to unit operations where at least a portion of the unit operation is in compression; and more particularly, to unit operations where at least a portion of the unit operation is contained within a pressure vessel and maintained in compression.

Prior art disclosures, such as U.S. Pat. No. 5,167,930, disclose a sealed chamber encasing a reactor, where the pressure within the sealed chamber equals that of the reactor. The equalization of pressures between reactor and chamber is maintained by providing an expandable reactor and an expandable sealed chamber that accommodated for such changes.

Other prior art disclosures, such as U.S. Pat. No. 3,515,520, disclose a reactor with an internal corrosion resistant sleeve adapted to receive a catalyst and/or a corrosive reactant therein. The sleeve is jacketed by a higher-pressure flow of a non-corrosive reactant to prohibit leaks in the sleeve from leaking the corrosive reactant and/or catalyst and making contact with the exterior reactor walls. The non-corrosive reactant enters the sleeve through an opening and exits via another opening in fluid communication with the catalyst/corrosive reactant and is thereafter consumed through the normal reaction process.

Still further prior art disclosures, such as U.S. Pat. No. 2,462,517, disclose a multiple walled reactor where an internal, first wall confines the reaction chamber, and a second wall defines a cavity occupied by a pressurized atmosphere, and a third wall defines a cavity occupied by a cooling fluid. The pressurized atmosphere is used to regulate the external reactor vessel pressure, while the cooling fluid is used to regulate the thermal energy within the pressurized reservoir and the reactor.

SUMMARY OF THE INVENTION

The present invention is directed to microchannel-based chemical processing unit operations. A first exemplary embodiment includes multiple microchannel processing unit operations ("microchannel process units") at least partially contained within a pressurized vessel. The pressurized nature of the vessel acts as a pressure balance upon the microchannel process units as the pressure exerted upon the exterior of the process units approximates the pressures exerted upon the interior of the process units by the processes carried out within the microchannels.

More specifically, the present invention includes microchannel process units that are removable from a pressurized vessel. An exemplary embodiment disclosed herein provides a pressurized vessel having conduits adapted to carry materials to and from the microchannel process units. In this manner, a docking structure associated with the vessel enables the process units to be removed, replaced, and/or reinstalled without requiring total or partial destruction of the pressurized vessel, the conduits, or the microchannel process units. In instances where one or more of the microchannel process units includes a microchannel reactor having catalyst retained within the microchannels, refurbishment of the catalyst can occur at a remote location from the vessel without utilizing the conduits of the vessel or requiring additional conduits to be constructed to provide access to the reactors through the vessel. In sum, the ability to remove and/or reinstall the microchannel process units from the pressure vessel simplifies the process for modifying, testing, and replacing the units prior to operation of the units within a pressurized environment, such as that provided by the vessel.

The present invention also includes an exemplary embodiment for carrying out a Fischer-Tropsch synthesis within a fixed or removable microchannel process unit housed at least partially within a pressurized vessel. Fischer-Tropsch synthesis reacts carbon monoxide and hydrogen in the presence of a catalyst to create higher molecular weight hydrocarbons. These higher molecular weight hydrocarbons provide the potential for partial solidification that might clog the microchannels of a microchannel process unit if the solids content of the streams is too great. To reduce the likelihood of a clog, the exemplary embodiment injects an elevated temperature fluid into the downstream sections of the microchannel process units to elevate the temperature of the product stream carrying the Fischer-Tropsch synthesis products to maintain a fluid flow within the microchannels. Before the elevated temperature fluid enters the microchannel process unit, a counter current heat exchanger is established between the conduit carrying the elevated temperature fluid and the conduit carrying the product of the Fischer-Tropsch synthesis so that farther downstream sections of the product conduit are contacted by higher elevated temperature fluid to ensure fluid flow. The exemplary embodiment also capitalizes upon the exothermic Fischer-Tropsch synthesis to provide steam for this or other processes within a chemical facility.

DETAILED DESCRIPTION

The exemplary embodiments of the present invention are described and illustrated below to include microchannel-based chemical process unit operations. The various orientational, positional, and reference terms used to describe the elements of the invention with respect to one another have been chosen with respect to a single point of reference for clarity and precision. Therefore, it will be understood that the positional and orientational terms used to describe the elements of the exemplary embodiments of the present invention are only used to describe the elements in relation to one another. Thus, variations envisioned by one of ordinary skill shall concurrently fall within the scope of the disclosure of this invention.

Figure 1:
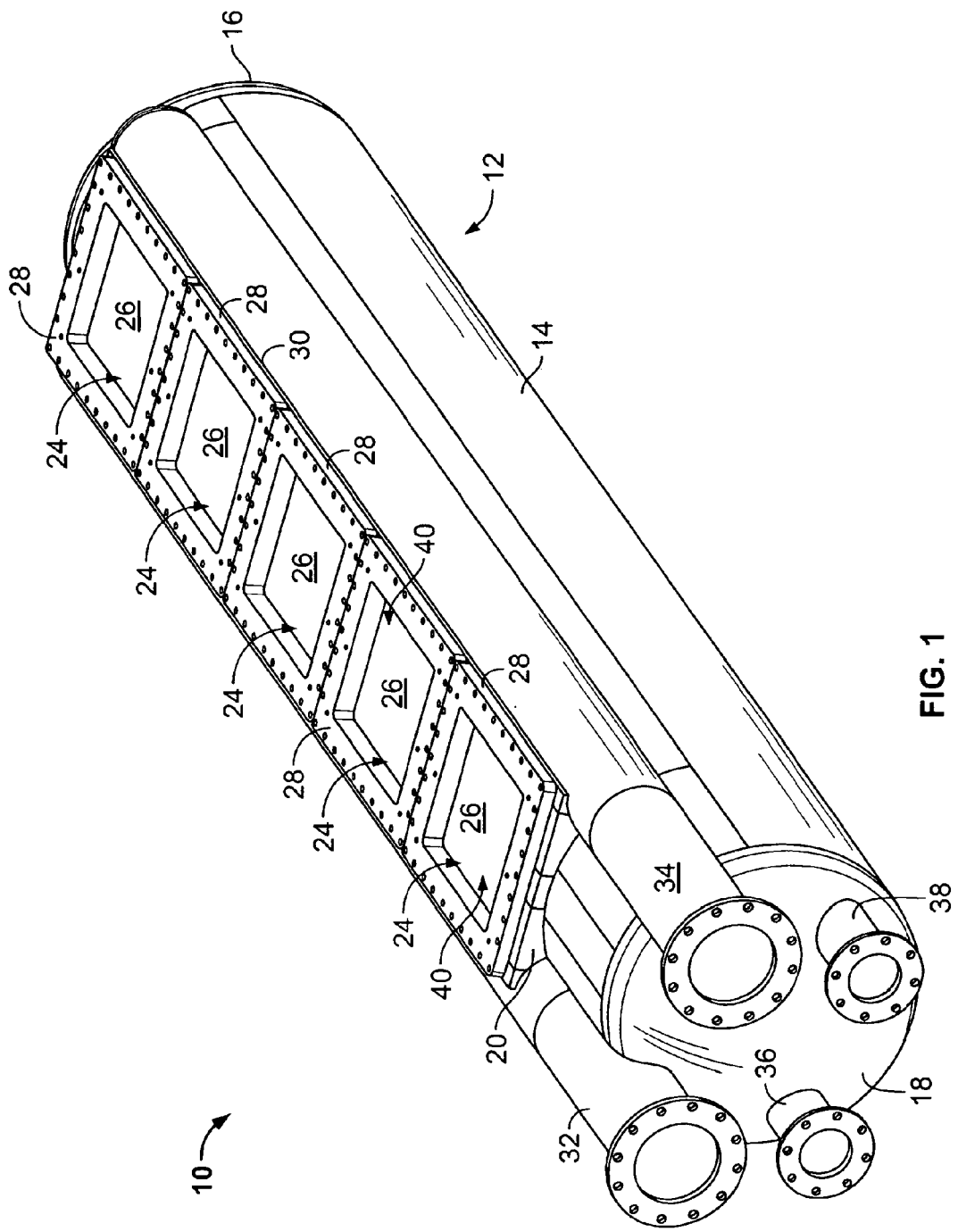
FIG. 1 is an elevated perspective view of a first exemplary embodiment of the present invention.
Figure 2:
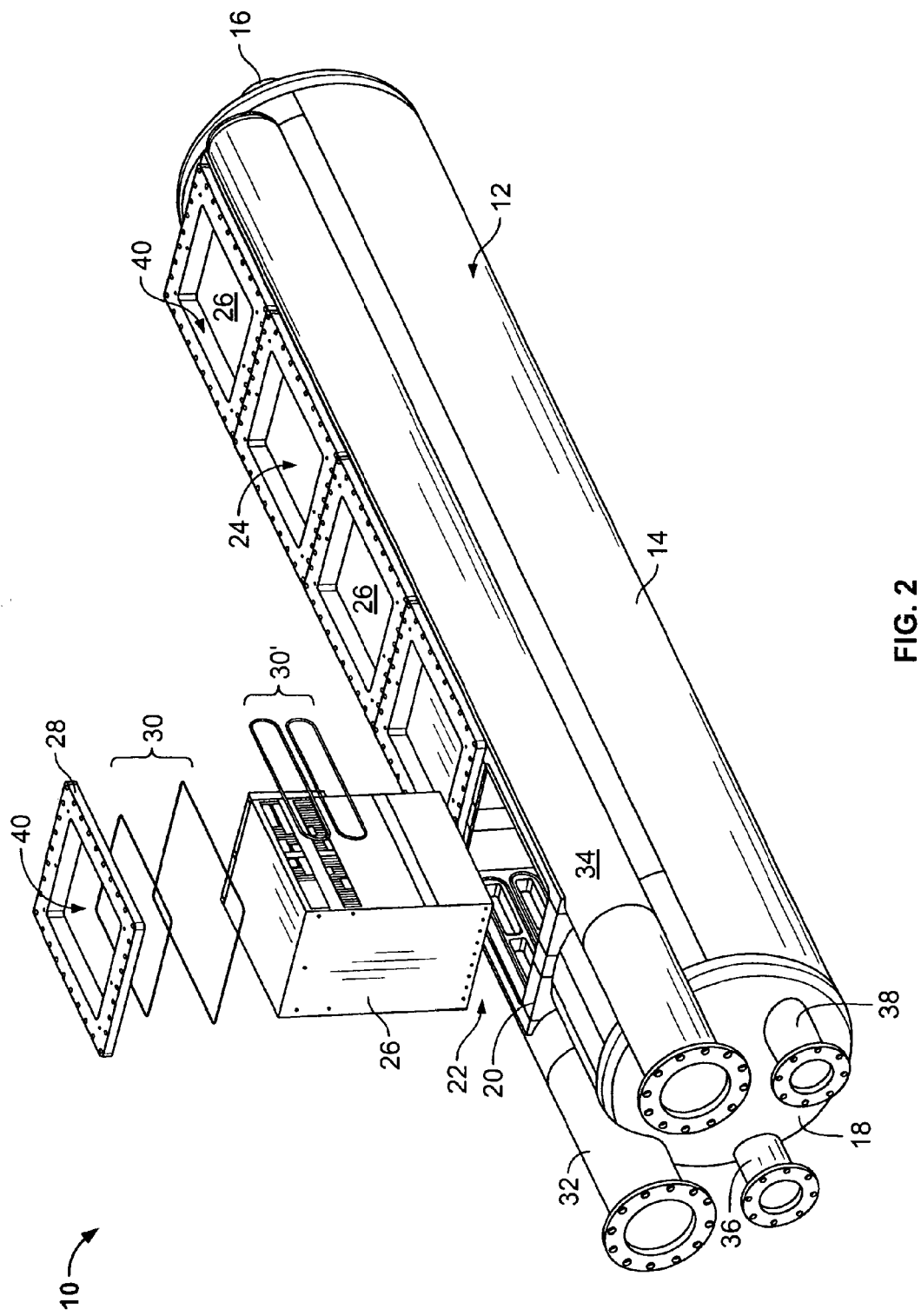
FIG. 2 is an elevated perspective view of the first exemplary embodiment with an exploded view of a microchannel process unit, flange, and gaskets.
Figure 3:
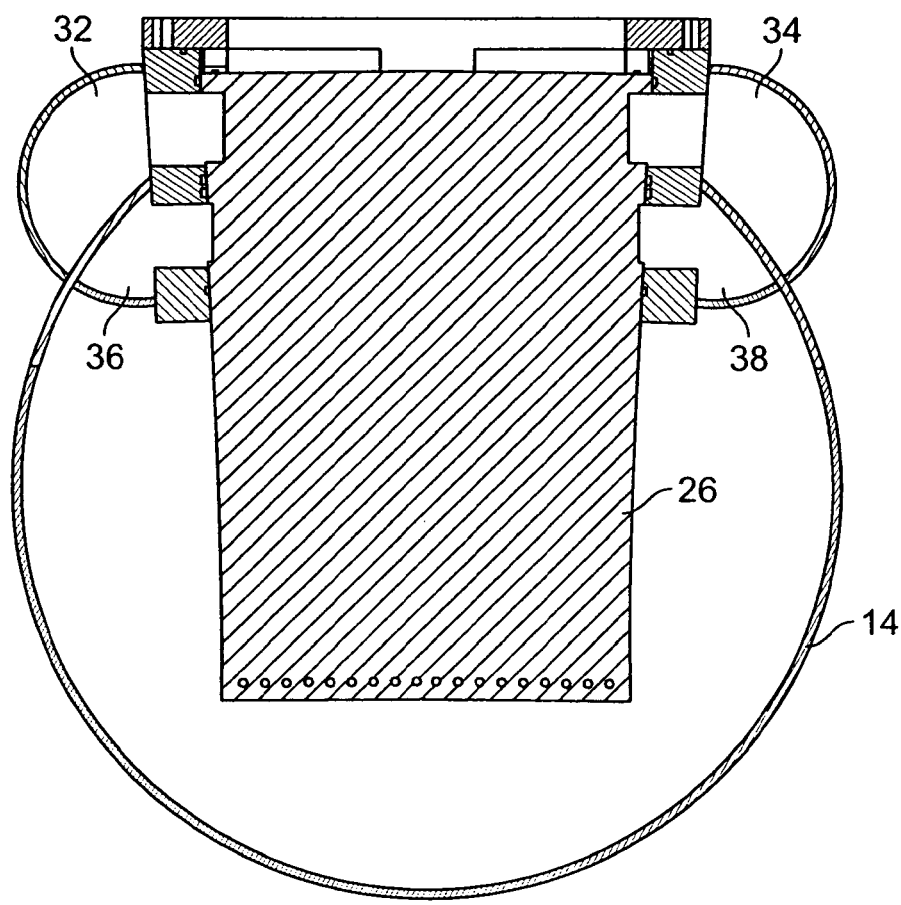
FIG. 3 is a cross-sectional view of the first exemplary embodiment.

Referring to FIGS. 1-3, a first exemplary embodiment of the present invention includes a microchannel unit operation assembly 10. The microchannel unit operation assembly 10 includes a cylindrical pressurized vessel 12 that defines an interior cavity bounded by a cylindrical wall 14 and two end caps 16, 18. An entrance orifice and an exit orifice (not shown) through the rear end cap 16 provide access to the interior cavity and are operative to supply or remove a pressurized fluid housed within the vessel 12. A dock 20 is mounted to the top of the vessel 12 and runs the majority of the longitudinal length of the vessel 12. The dock 20 circumscribes a rectangular opening 22 within the cylindrical wall 14 and defines five generally rectangular openings 24 that are operative to receive five removable microchannel process units 26. As will be discussed in more detail below, the microchannel process units 26 include at least one side that is tapered and adapted to rest upon a correspondingly tapered surface of the clock 20. Thereafter, a rectangular flange 28 bolts to the dock 20 (and optionally to the unit 26) and is operative to sandwich a gasket assembly 30, 30' between each process unit 26 and the dock 20. The first gasket assembly 30 is operative to seal the rectangular opening in the dock 20 occupied by the microchannel process units 26 and seal an interface between the flange 28 and each process unit 26, while the second gasket assembly 30' is operative to seal the interface between the openings within the process unit 26 and the openings on the side of the dock 20.

A series of conduits 32, 34, 36, 38 are mounted to the vessel 12 and are adapted to direct fluid streams into, or away from, each of the microchannel process units 26. Each microchannel process unit 26 includes a series of microchannels adapted to be in fluid communication with the conduits mounted to the vessel 12. Three of the conduits 32, 34, 36 are operative to carry input streams, while one conduit 38 carries an output stream. A second output stream is exhausted at the top of each microchannel process unit 26 through the rectangular opening 40 in the flange 28 and gasket assembly 30.

For purposes of explanation only, the microchannel process unit 26 includes a microchannel reactor 26 operative to carry out two concurrent reactions. While various reactions may be carried out within a microchannel reactor 26, for purposes of explanation, it is presumed that the microchannel reactor 26 will carry out a combustion reaction and a syngas reaction (where methane and stream are reacted to generate primarily carbon monoxide and hydrogen gas). In such an exemplary combustion reaction, a fluid fuel stream, which may consist of carbon dioxide, hydrogen, methane, and carbon monoxide, is carried through the first input conduit 32 and directed to a first set of microchannels within the reactor 26. The second input conduit 34 is operative to carry an oxygen-rich fluid, which may consist of air, that is directed to a second set of microchannels within the reactor 26. The second set of microchannels is operative to direct the oxygen-rich fluid into direct contact with the fuel stream flowing within a downstream section of the first set of microchannels. This downstream section includes distributed catalyst that facilitates a combustion reaction between the oxygen-rich fluid and the fuel stream generating thermal energy and reaction products. The catalyst may line the walls of the downstream section of the first set of microchannels or be retained within the microchannels in another manner.

The downstream section of the first set of microchannels is in intimate contact with a third set of microchannels containing a reactant stream delivered thereto by the third input conduit 36. The reactant stream includes a pressurized mixture of steam and methane that utilize the thermal energy generated by the combustion reaction, in the presence of a catalyst, to drive an endothermic syngas (steam reformation) reaction where the product stream is rich in hydrogen gas. The exhaust of the combustion reaction is vented through openings 40 within the top of the reactor 26, while the steam reformation products are directed out of the reactor 26 and into the first output stream 38 for further processing downstream. Exemplary pressures exerted upon the microchannels of the reactor for these reactions include pressures at or above 335 psig. In order to reduce the stress upon the microchannels, the reactors 26 are at least partially surrounded by a pressurized fluid within the vessel 12 operative to provide a pressure balance by exerting a pressure of approximately 335 psig. In order to exert such pressures upon the exterior of the reactors 26, the pressurized vessel 12 must be fabricated to withstand these pressures for extended periods. The following is an exemplary sequence to fabricate the pressurized vessel 12 and associated conduits 32, 34, 36, 38 in accordance with the present invention, based upon a cylindrical vessel 12 having a diameter of thirty-six inches.

Figure 4:
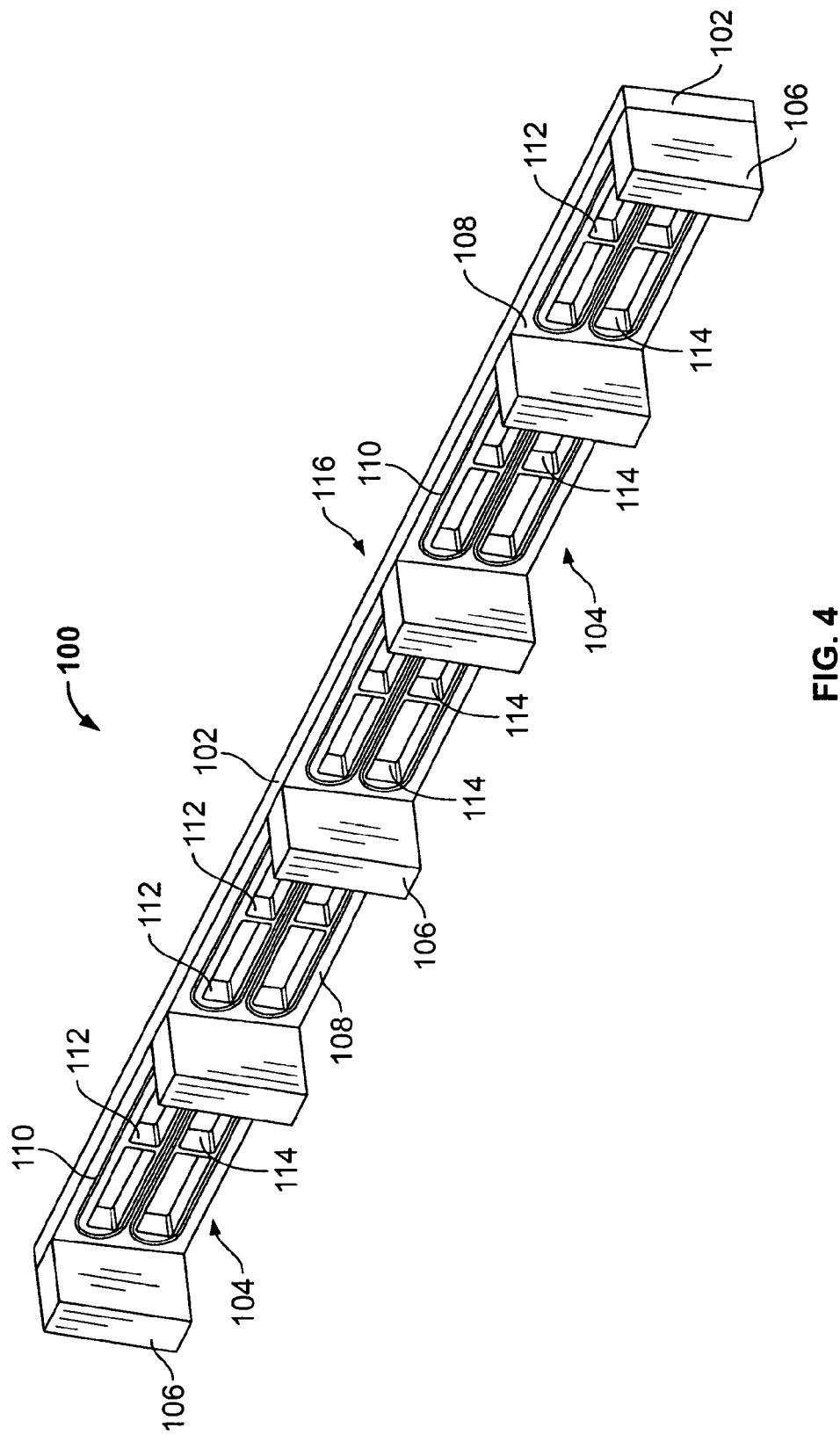
FIG. 4 is an elevated perspective view of a first exemplary structure for use in fabricating the first exemplary embodiment.

Referring to FIG. 4, a preliminary frame 100 includes a rectangular metal bar 102 having five sets of four dove-tailed rectangular openings 104 formed therethrough that are each separated by a series of metal blocks 106. Exemplary dimensions for the bar 102 include 160 inches in length, 12.15 inches in width, and 2.38 inches in thickness, while exemplary dimensions for each block 106 include 4.00 inches in length, 12.15 inches in width, and 7.24 inches in thickness. The metal blocks 106 are mounted to an interior surface 108 of the bar 102 at a predetermined angle that, as will be discussed below, can vary between ±45 degrees from perpendicular. Each of the four rectangular openings 104 has a dimension of 27.19 inches length, 12.15 inches width with the depth corresponding to the thickness of the bar. Ten sets of gasketing material 110 are mounted to a channel (not shown) within the interior surface 108 of the bar 102, with each set of gasketing material 110 surrounding two (top two 112 or bottom two 114) of the four dove-tailed openings 104. Exemplary gasketing material 110 for use with the present invention includes, without limitation, Garlock Helicoflex Spring Energized Seals, metal/graphite gaskets, reinforced graphite, corrugated metal/spiral wound gaskets, and elastomeric seals. As discussed previously, the gasketing material 110 is operative to provide a fluidic seal between the interior surface 108 of the bar 102 and an exterior surface of the microchannel process unit (see FIG. 2, 30'). Two mirror image frames 100 are constructed so that the metal blocks 106 of each frame face one another and the exterior surfaces 116 of each bar 102 face away from one another.

Figure 5:
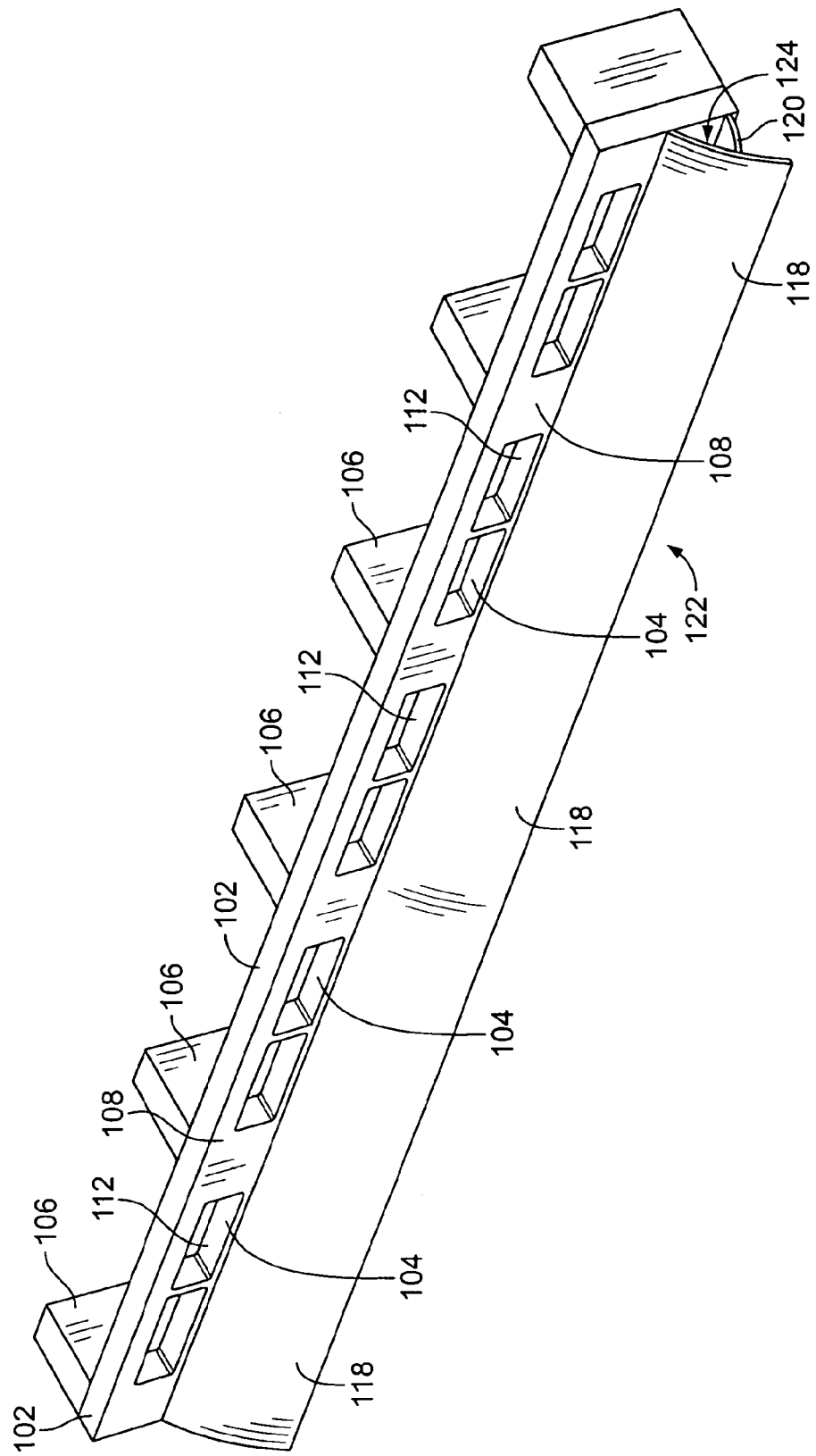
FIG. 5 is an elevated perspective view of a second exemplary structure for use in fabricating the first exemplary embodiment.
Figure 6:
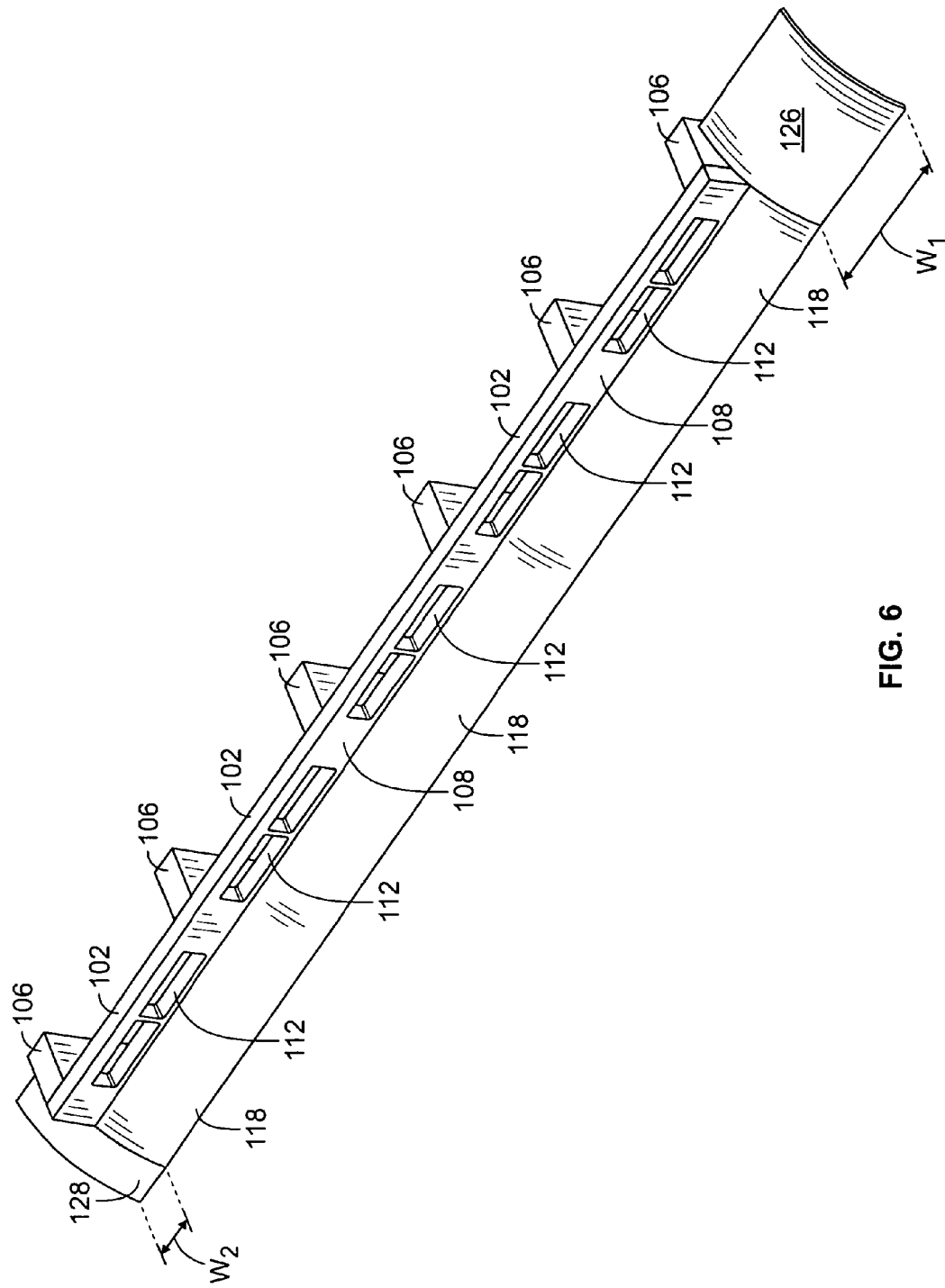
FIG. 6 is an elevated perspective view of a third exemplary structure for use in fabricating the first exemplary embodiment.

Referencing FIGS. 5 and 6, an arcuate metal strip 118 is welded to the exterior surface 116 of each bar 102. As will be apparent below, the metal strip 118 is incorporated into the overall structure to define the cylindrical vessel 12 (see FIG. 1) and, therefore, has an arc representative of a 9.69 inch wide longitudinal section of a thirty-six inch cylinder. The metal strip 118 runs the entire length of the bar 102 and is operative to divide the top two 112 and bottom two 114 rectangular openings 104. A 10 inch pipe segment 120 is welded to the underneath side 122 of the strip 118 and welded to the exterior surface 116 of the bar 102 to create a longitudinal conduit 124 supplying the bottom 114 openings. Two arcuate extensions 126, 128 are aligned with the ends of the metal strip 118 and welded to respective ends of the frame 100, which includes mounting the extensions 126, 128 to the ends of the strip 118, bar 102, and block 106. The arcuate extensions 126, 128 are representative of a 19.65 inch segment of a thirty-six inch diameter cylinder, with the first extension 126 having a width W1 of 20.00 inches, and the second extension 128 having a width W2 of 6.00 inches.

Figure 7:
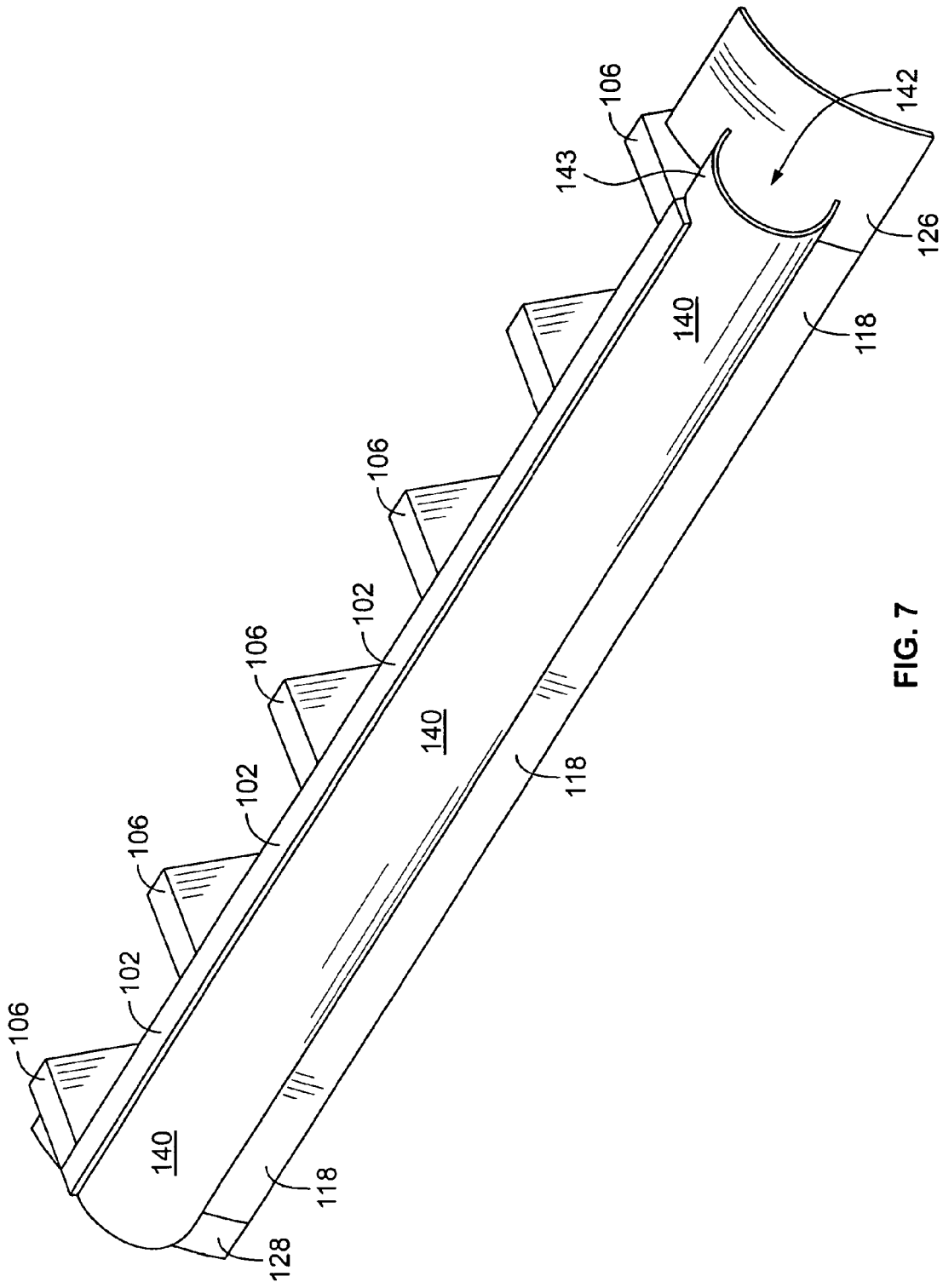
FIG. 7 is an elevated perspective view of a fourth exemplary structure for use in fabricating the first exemplary embodiment.

Referencing FIG. 7, a ten inch pipe segment 140 is welded to the exterior 116 of the bar 102, the strip 118, the block 106, and the extensions 126, 128 to provide a separate longitudinal conduit 142 feeding the top 112 series of openings. This conduit 142 runs in parallel with the conduit 124 feeding the bottom two 114 series of openings. A notch is cut from the segment 140 prior to welding in order to allow the front aspect 143 to match the contours of the ends of the bar 102, the block 106, and top surface of the first extension 126.

Figure 8:
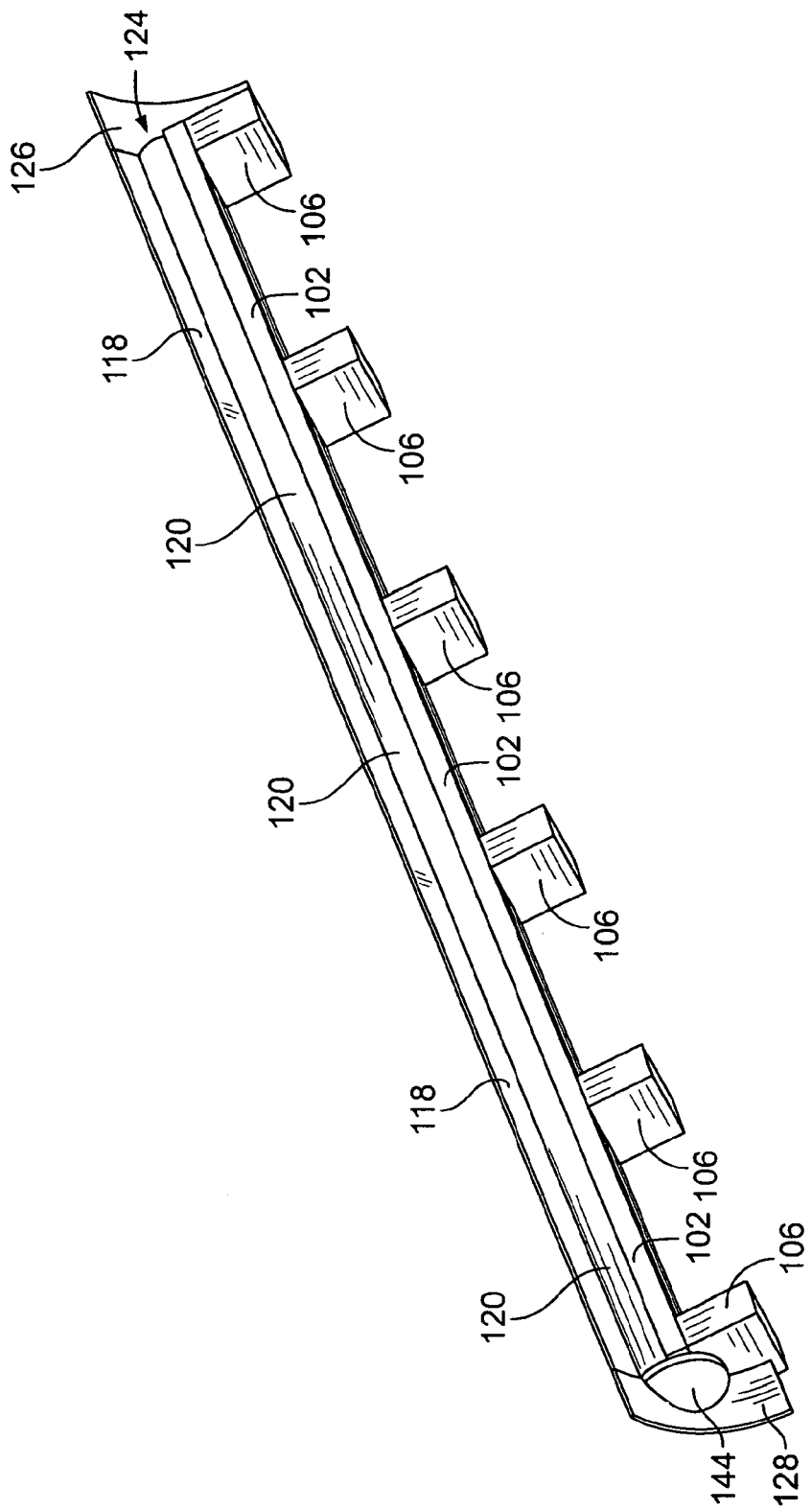
FIG. 8 is an elevated perspective view of a fifth exemplary structure for use in fabricating the first exemplary embodiment.
Figure 9:
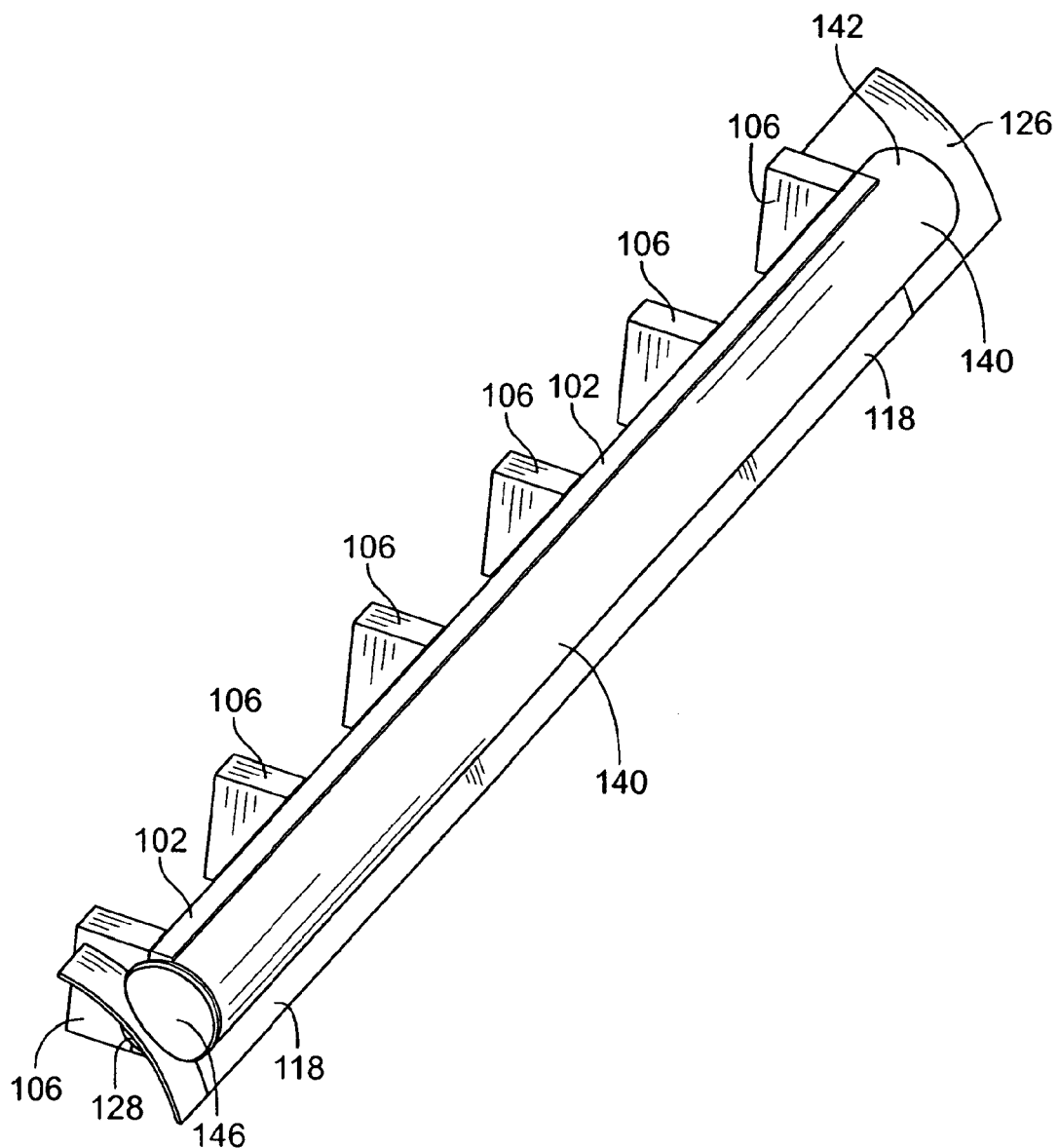
FIG. 9 is an elevated perspective view of a sixth exemplary structure for use in fabricating the first exemplary embodiment.

Referencing FIGS. 8 and 9, end caps 144, 146 contacting the ends of the two respective segments 120, 140, the bar 102, and the far block 106 are welded above and below the second extension 128 in order to enclose the ends of the conduits 124, 142.

Figure 10:
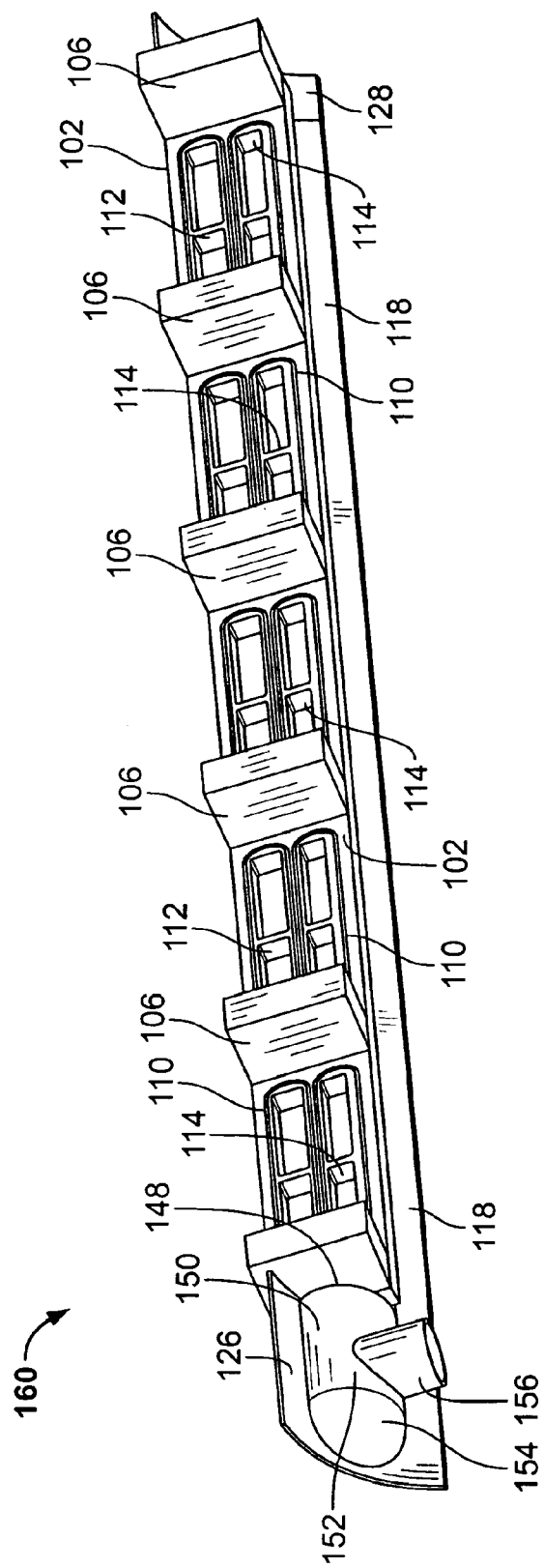
FIG. 10 is an elevated perspective view of a seventh exemplary structure for use in fabricating the first exemplary embodiment.

Referring to FIG. 10, an opposing end 148 of the first conduit 124 receives an adapter 150 operative to redirect the flow of materials in a direction other than along the linear longitudinal length of the bar 102. The adapter 150 comprises a ten inch pipe segment 152 and an end cap 154 contoured to match the arc of the underside of the first extension 126. A six inch pipe segment 156 is circumferentially welded to an orifice (not shown) in the ten inch pipe segment 152 to provide a down tube. The resulting structure comprises an intermediate frame 160.

Figure 11:
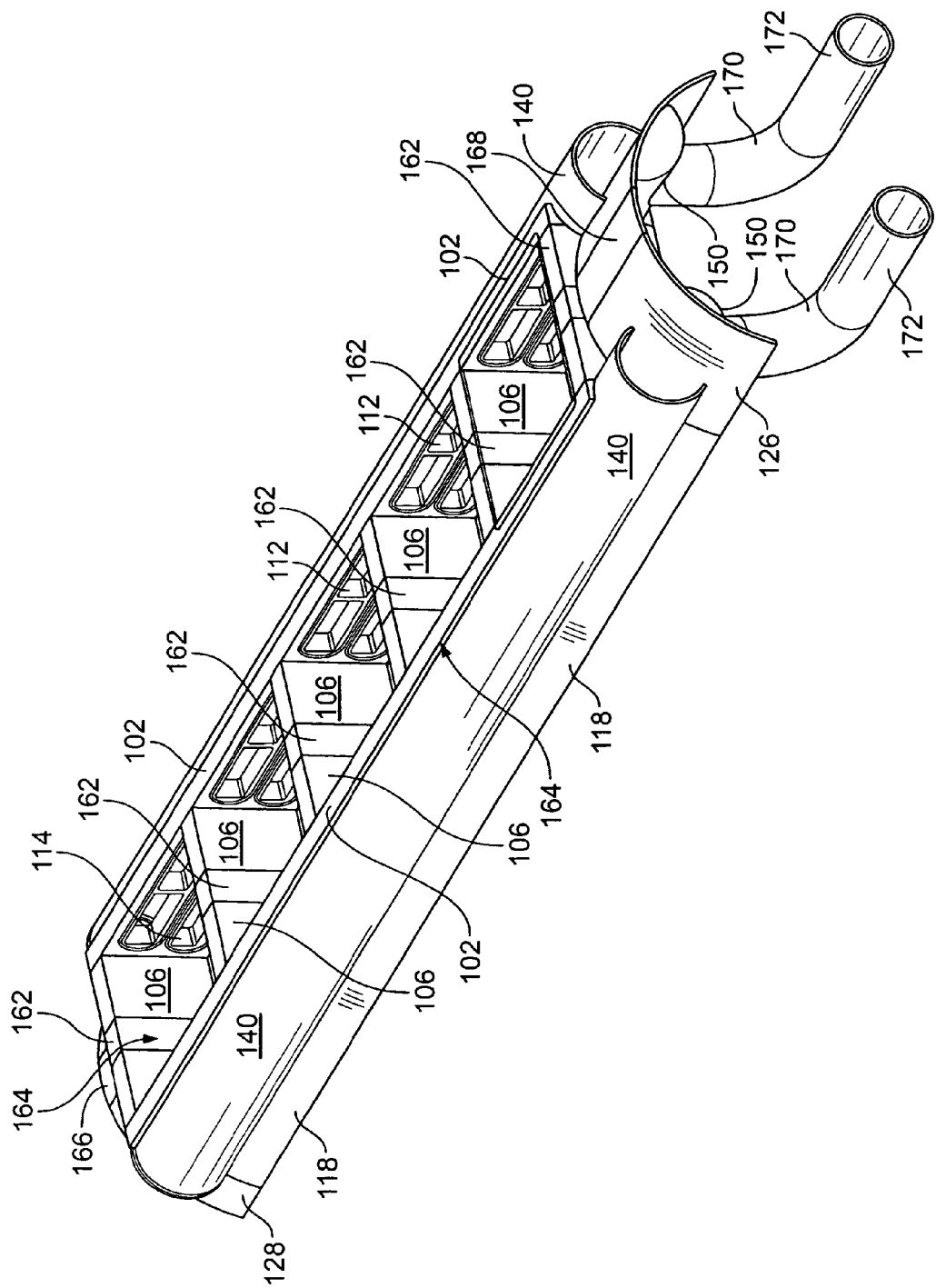
FIG. 11 is an elevated perspective view of an eighth exemplary structure for use in fabricating the first exemplary embodiment.
Figure 12:
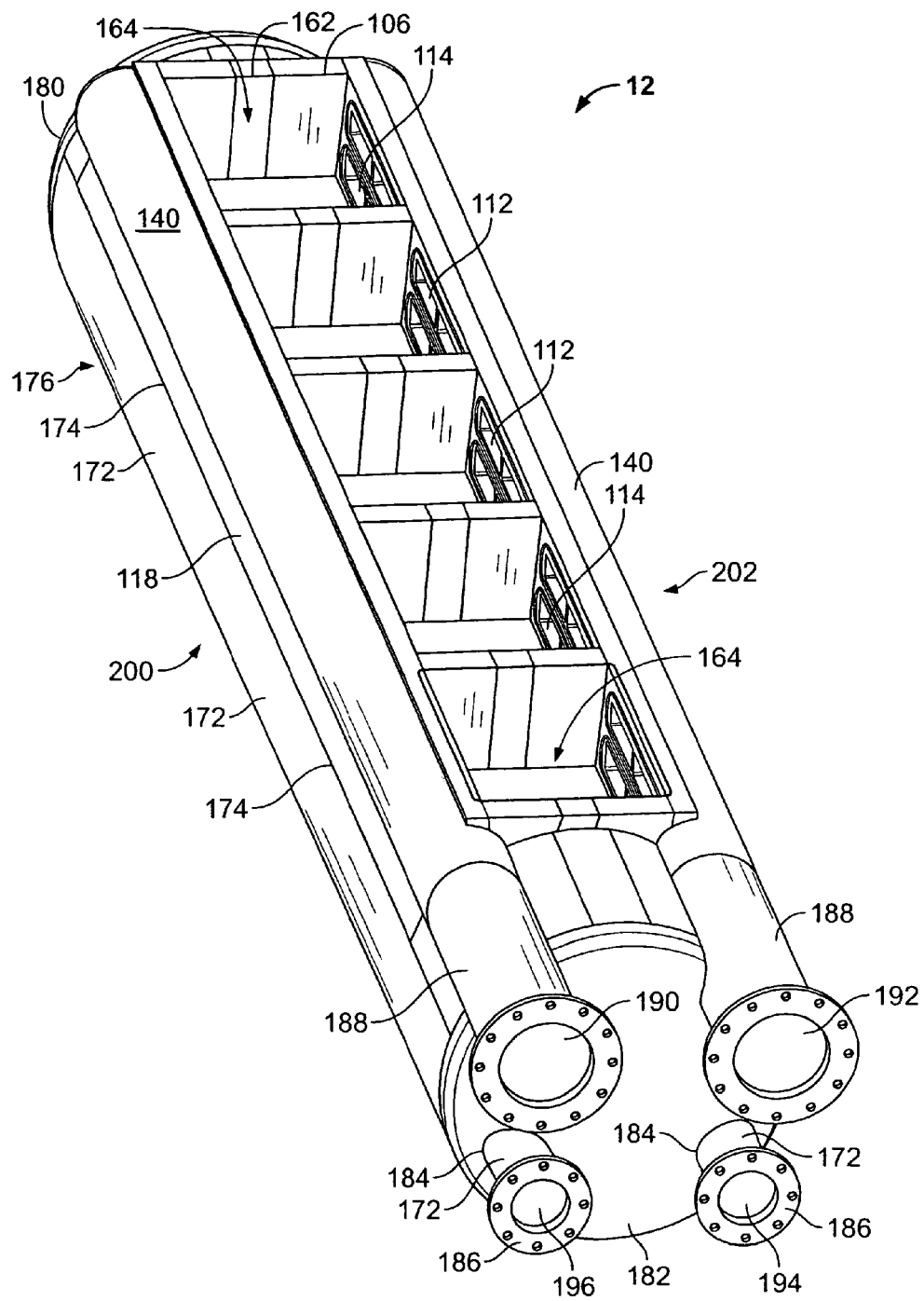
FIG. 12 is an elevated perspective view of the first exemplary embodiment without the microchannel process units installed.

Referencing FIG. 11, the two, mirror image intermediate frames 160 are joined by welding a series of block spacers 162 between opposing blocks 106, resulting in five rectangular openings 164 within the top of the eventual vessel 12 (see FIG. 12). A corresponding spacer 166, 168 is welded between the extensions 126,128 and to the block spacers 162 and opposing blocks 106 in order to bridge the gap between the extensions. An elbow pipe 170 is welded to the circumferential opening of each adapter 150, where the elbow pipe has an extension pipe 172 welded thereto.

Referring to FIG. 12, a semicircular pipe 172 is welded to the opposing ends 174 of each strip 118 and extensions 126, 128 to provide a continuous cylindrical body 176 (outside of the openings 154). A rear end cap 180 and a front end cap 182 are welded to the cylindrical body 176 to enclose the 36 inch diameter opening on each end. The rear end cap 180 includes two flanged pipes (not shown) providing fluid communication with the interior of the vessel 12. The front end cap 182 includes two orifices 184 adapted to allow the pair of extension pipes 172 to pass therethrough as the cap is oriented to abut the opening at the front of the cylindrical body 176. A first circumferential weld mounts the body 176 to the rear cap 180, and a second circumferential weld mounts the front cap 182 to the body 176. A third set of circumferential welds is operative to close the front end of the vessel 12 by sealing any gap between the openings 184 and the extension pipes 172 piercing the openings 184. A flange 186 is mounted to each end of the respective extension pipes 172 and is adapted to mate with a preexisting flanged conduit (not shown). Two ten inch flanged pipes 188 are respectively contoured to match the exterior shape of the vessel 12 and welded to the ends of the pipe sections 140 and to the exterior of the vessel 12. The flanges at the end of the pipe 188 are adapted to mate with a preexisting flanged conduit (not shown) upon installation of the vessel 12.

The resulting vessel 12 is operative to provide sealed fluid communication between the flanged openings 190, 192, 194, 196 and the openings 112, 114 along the interior sides of the vessel 12. More specifically, the first flanged opening 190 provides the sealed conduit 32 (see FIG. 1) in fluid communication with the top openings 112 longitudinally spaced along the left hand side 200 of the vessel, whereas the second flanged opening 192 provides the sealed conduit 34 (see FIG. 1) in fluid communication with the top openings 112 longitudinally spaced along the right hand side 202 of the vessel. The third flanged opening 194 provides the sealed conduit 38 (see FIG. 1) in fluid communication with the bottom openings 114 longitudinally spaced along the right hand side 202 of the vessel, whereas the fourth flanged opening 196 provides the sealed conduit 36 (see FIG. 1) in fluid communication with the bottom openings 114 longitudinally spaced along the left hand side 200 of the vessel.

As discussed above, the orientation of the blocks 106 with respect to the bar 102 may be manipulated during fabrication to angle the openings 112, 114 with respect to completely vertical, such as tapering the openings 112, 114 inward (from bottom to top) or tapering the openings 112, 114 outward (from bottom to top). Other methods operative to angle the openings with respect to completely vertical will become obvious to those of ordinary skill, and all such methods and apparatuses concurrently fall within the scope of the present invention. By manipulating the dimensions of the opening 164, is it possible to suspend the microchannel process unit 26 within the opening. For example, if each bar 102 is oriented outward 5 degrees (from bottom to top) from vertical, a V-shaped profile is provided along at least one plane of the opening 164 (see FIG. 3). If the microchannel process unit 26 is correspondingly shaped to taper inward from top to bottom to match the taper of the opening 164, it is possible to vertically suspend the reactor from the dock 20 without requiring the process unit 26 to be rigidly mounted to the dock, such as by welding.

Figure 13:
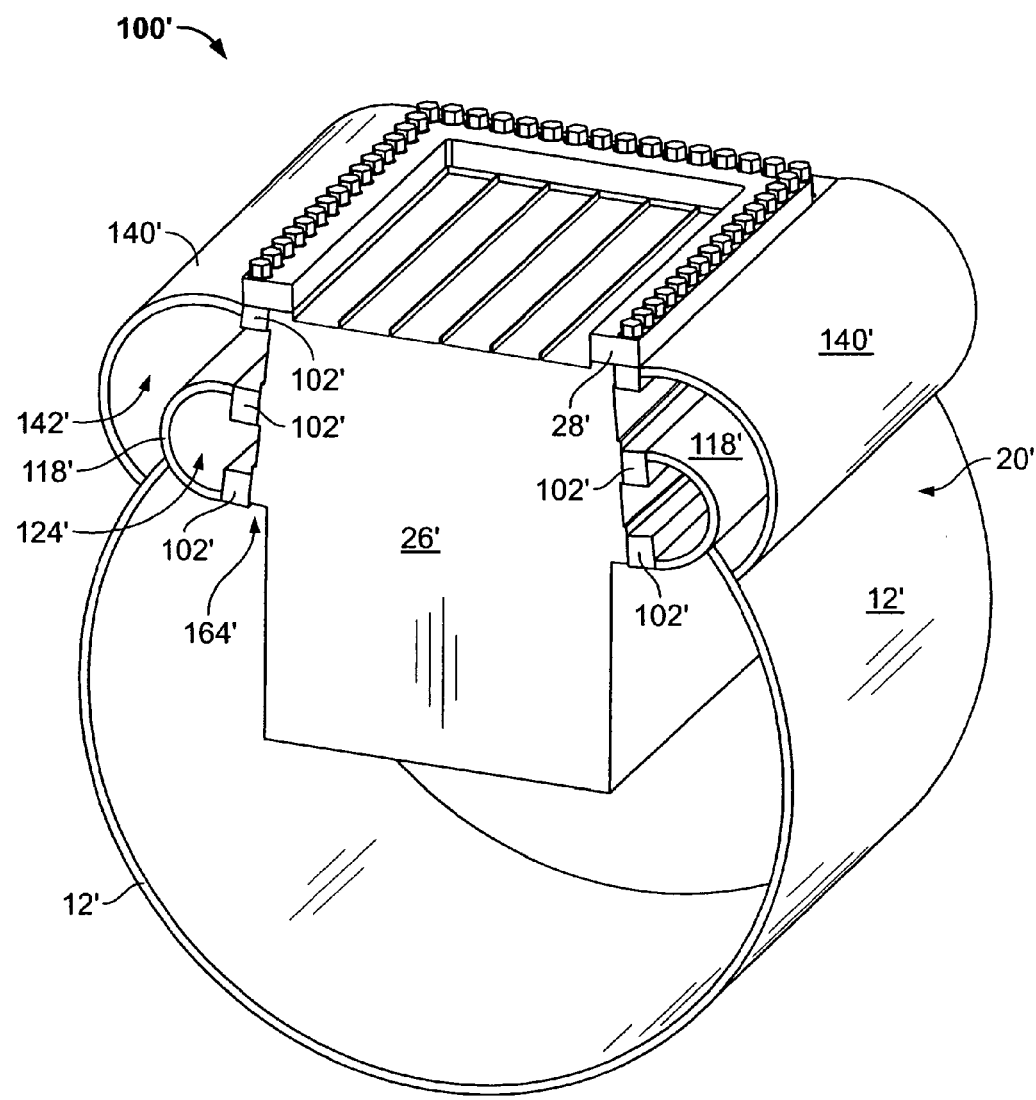
FIG. 13 is an elevated cross sectional view of a first alternate exemplary embodiment.

Referring to FIG. 13, an alternate configuration 100' may be utilized in instances where the operating pressure exerted upon the process unit 26' by the fluid within the vessel 12' will be a positive gauge pressure, tending to push the process unit 26' out of the opening 164', it may be advantageous to orient each bar 102' inward 5 degrees (from bottom to top) from vertical to provide an inverted V-shaped profile or frustropyramidal portion is provided along at least one plane of the opening 164' so that higher pressures tend to push a process unit 26' with a correspondingly inverted V-shaped profile more tightly against the dock 20'. In such an instance, the process unit 26' may include a flange 28' or other attachment point to mount the unit 26' to the dock/vessel 20'/12'. It is to be understood either approach (tapered inward or tapered outward) could be utilized in conditions calling for positive or negative operational gauge pressures to be exerted upon the process unit 26, 26' by the contained fluid of the vessel 12, 12'.

Several advantages are apparent from the exemplary embodiments of the present invention. For example, by making the microchannel process unit 26 removable from the vessel 12, replacement of the units 26 is made much easier, as opposed to prior methods requiring cutting the welds between the units and the vessel 12. Welding of the units 26 also introduced high local temperatures that tended to degrade or destroy catalyst in proximity to the weld and/or result in delaminations. In addition, by making the units 26 removable by simply twisting a few bolts, refurbishment of catalyst within the reactor units may be accomplished without the need for separate catalyst refurbishment lines piercing the pressure vessel 12 and units.

Other advantages of making the microchannel process units 26 removable include the removal or replacement of individual units 26 (as opposed to a bank of units), the ability to refurbish active metal catalysts away from the pressure vessel 12, and the ability to pressure test or perform other tests upon the process unit 26 away from the pressure vessel 12.

Figure 14:
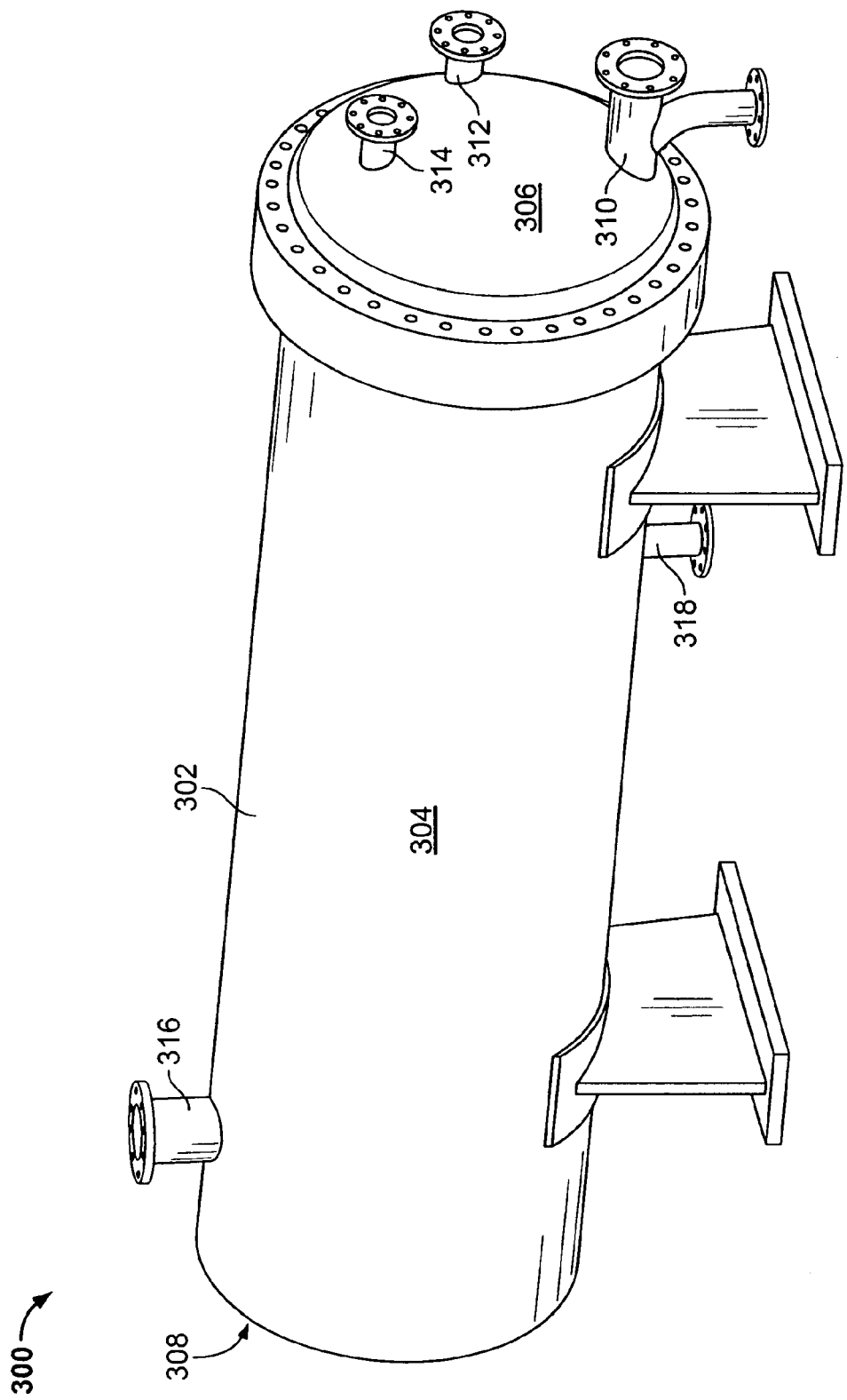
FIG. 14 is an elevated perspective view of a second exemplary embodiment.
Figure 15:
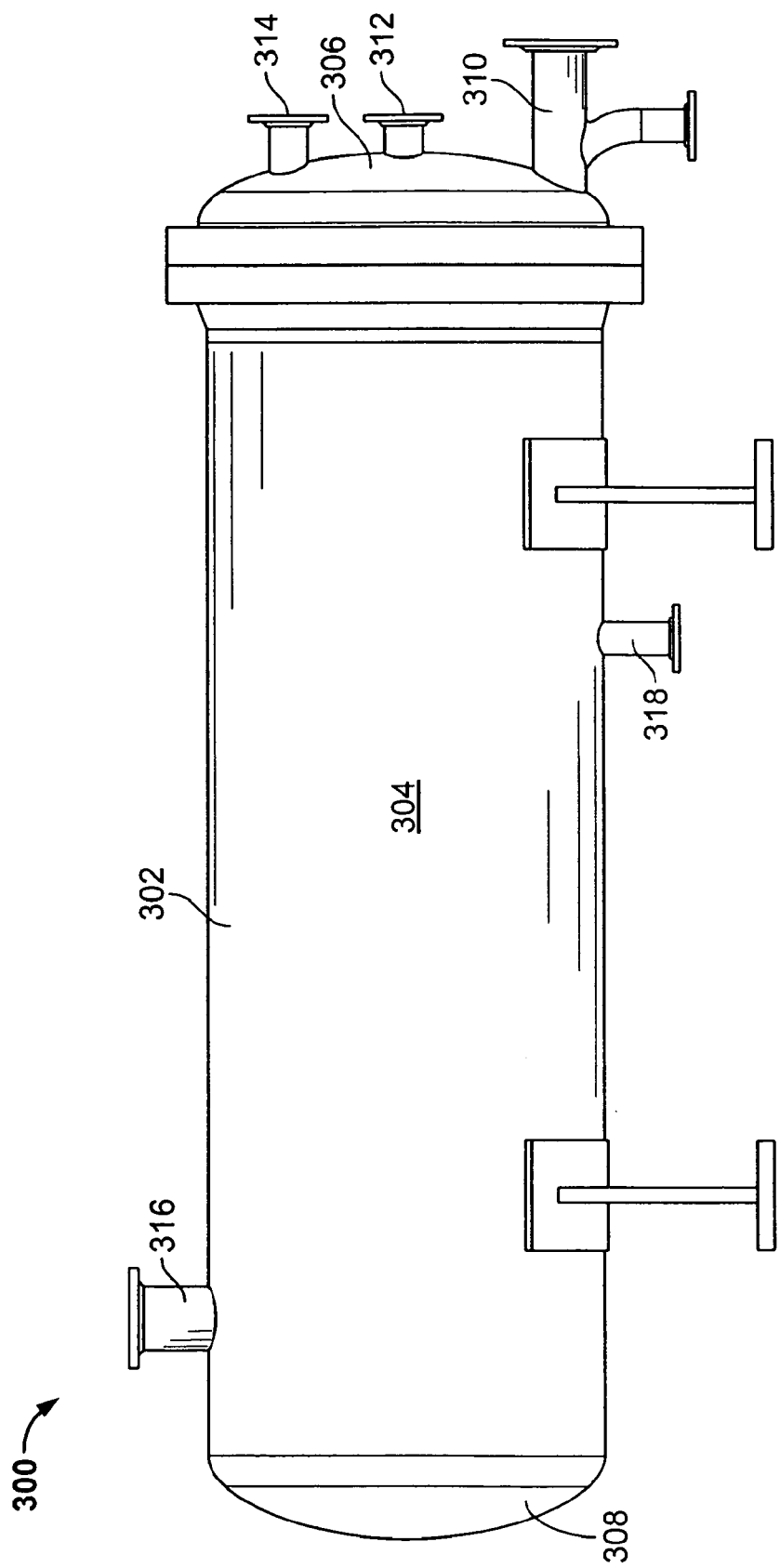
FIG. 15 is a right-side view of the second exemplary embodiment of FIG. 14.
Figure 16:
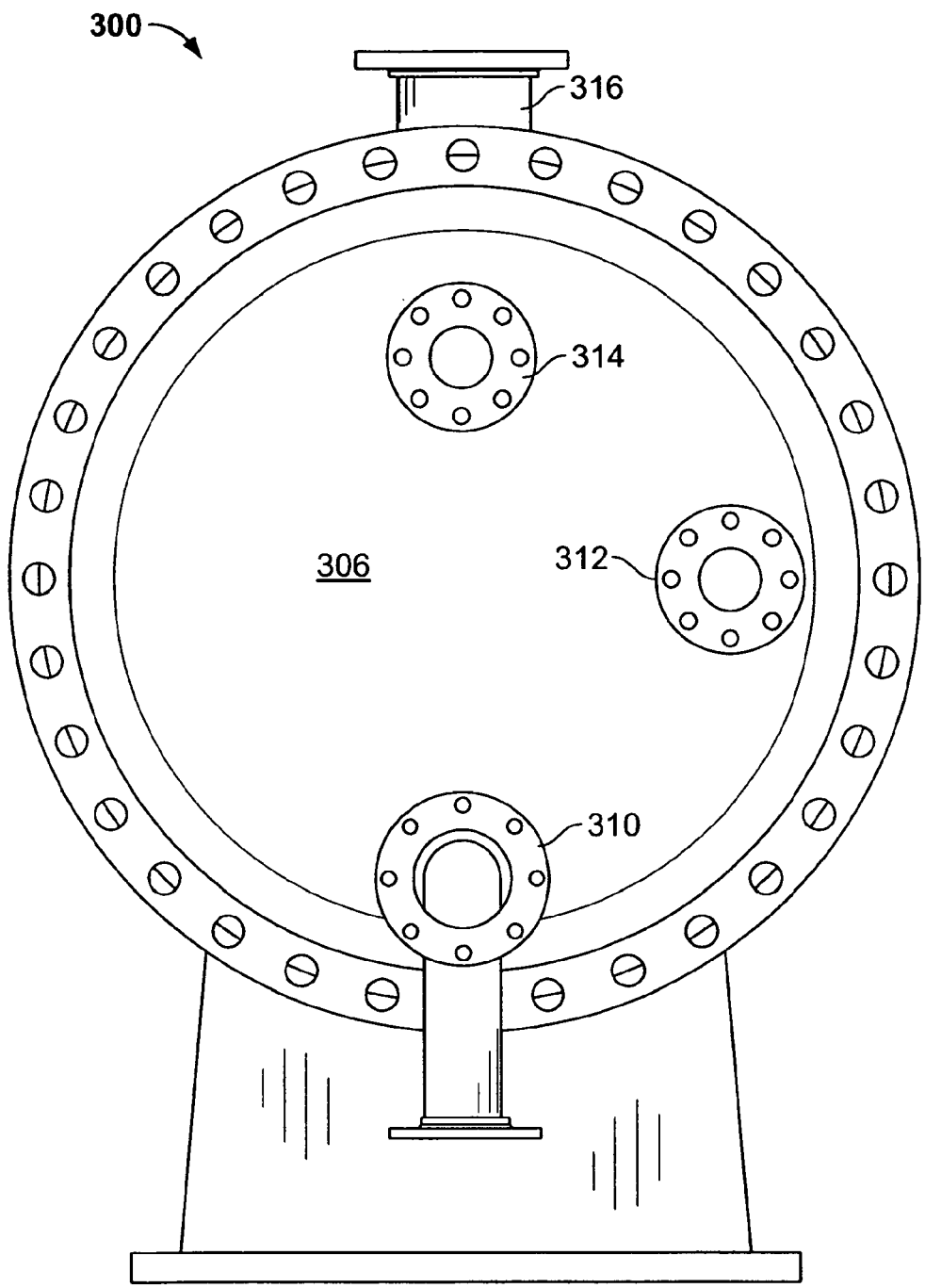
FIG. 16 is a frontal view of the second exemplary embodiment of FIG. 14.

Referencing FIGS. 14-16, a second exemplary embodiment of the present invention includes a Fischer-Tropsch reactor assembly 300. The reactor assembly includes a pressurized vessel 302 consisting of a hollow cylindrical shell 304 sealed at its ends by a front end cap 306 and a rear end cap 308. The front end cap 306 includes three orifices that receive three corresponding flanged conduits 310, 312, 314 that extend into the interior of the shell 304. Two other flanged conduits 316, 318 are received by two orifices within the shell 304 and provide communication with the interior of the shell. Each end cap 306, 308 is mounted circumferentially to the cylindrical shell to provide a fluid tight seal therebetween. Exemplary techniques for mounting the end caps 306, 308 to the cylindrical shell 304 include, without limitation, welding and flanged connections utilizing torqued bolts. Each flanged conduits 310, 312, 314, 316, 318 is circumferentially welded to a corresponding opening within the vessel 302 in order to mount the conduits to the vessel and ensure the vessel is capable of being pressurized and maintaining such pressure.

For purposes of explanation only, the Fischer-Tropsch reactor assembly 300 is adapted to carry out a Fisher-Tropsch synthesis where carbon monoxide and hydrogen within a feed stream are converted into higher molecular weight hydrocarbons in the presence of a catalyst. More specifically, the higher molecular weight hydrocarbons include $C_{5-100}$ paraffins, oxygenates, and olefins. In order to increase the yield of desired products, the dissipation of thermal energy away from the reactive zones of a Fischer-Tropsch reactor is important, as the reaction is highly exothermic.

Figure 17:
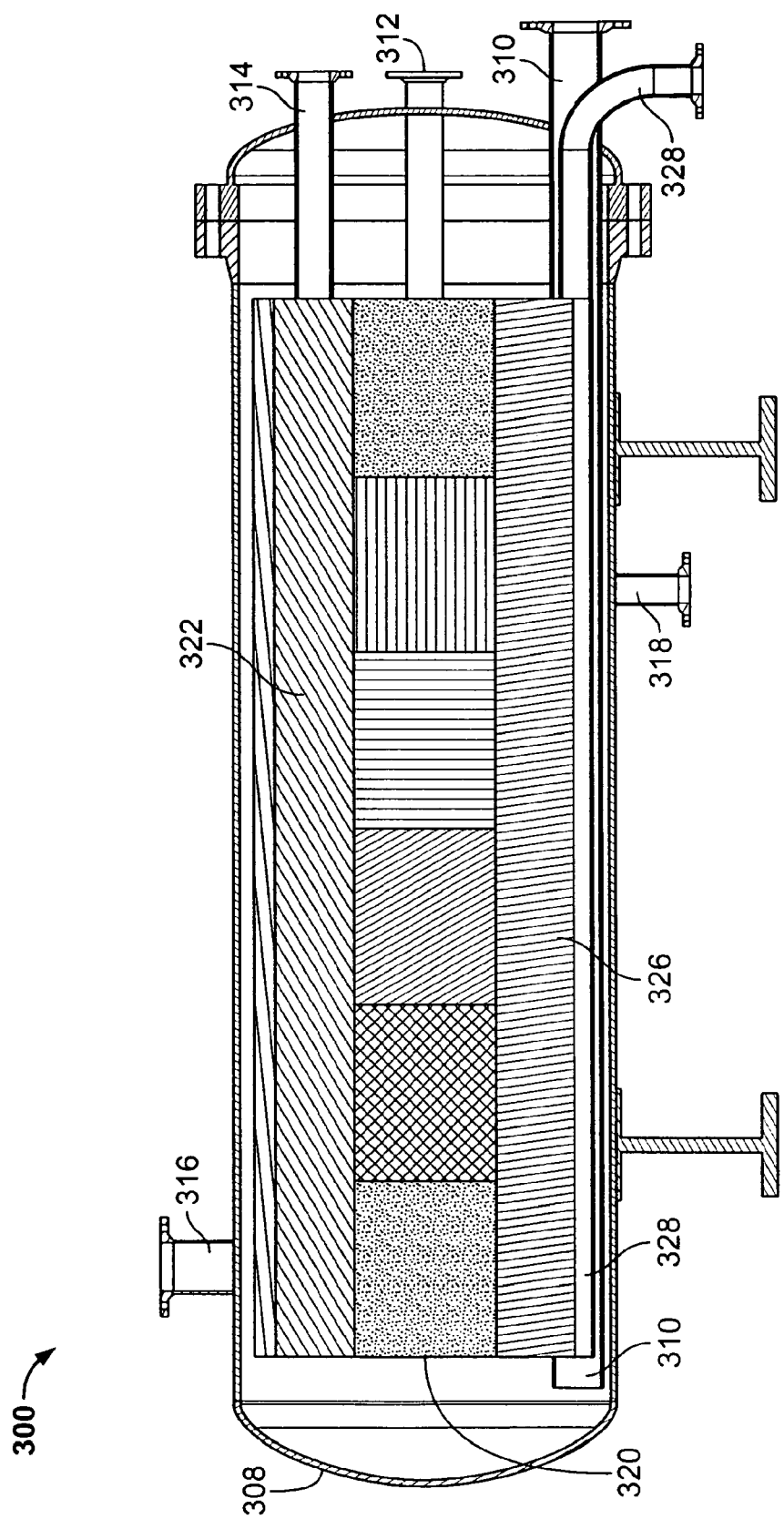
FIG. 17 is a right-side, cross-sectional view of the second exemplary embodiment of FIG. 14.
Figure 18:
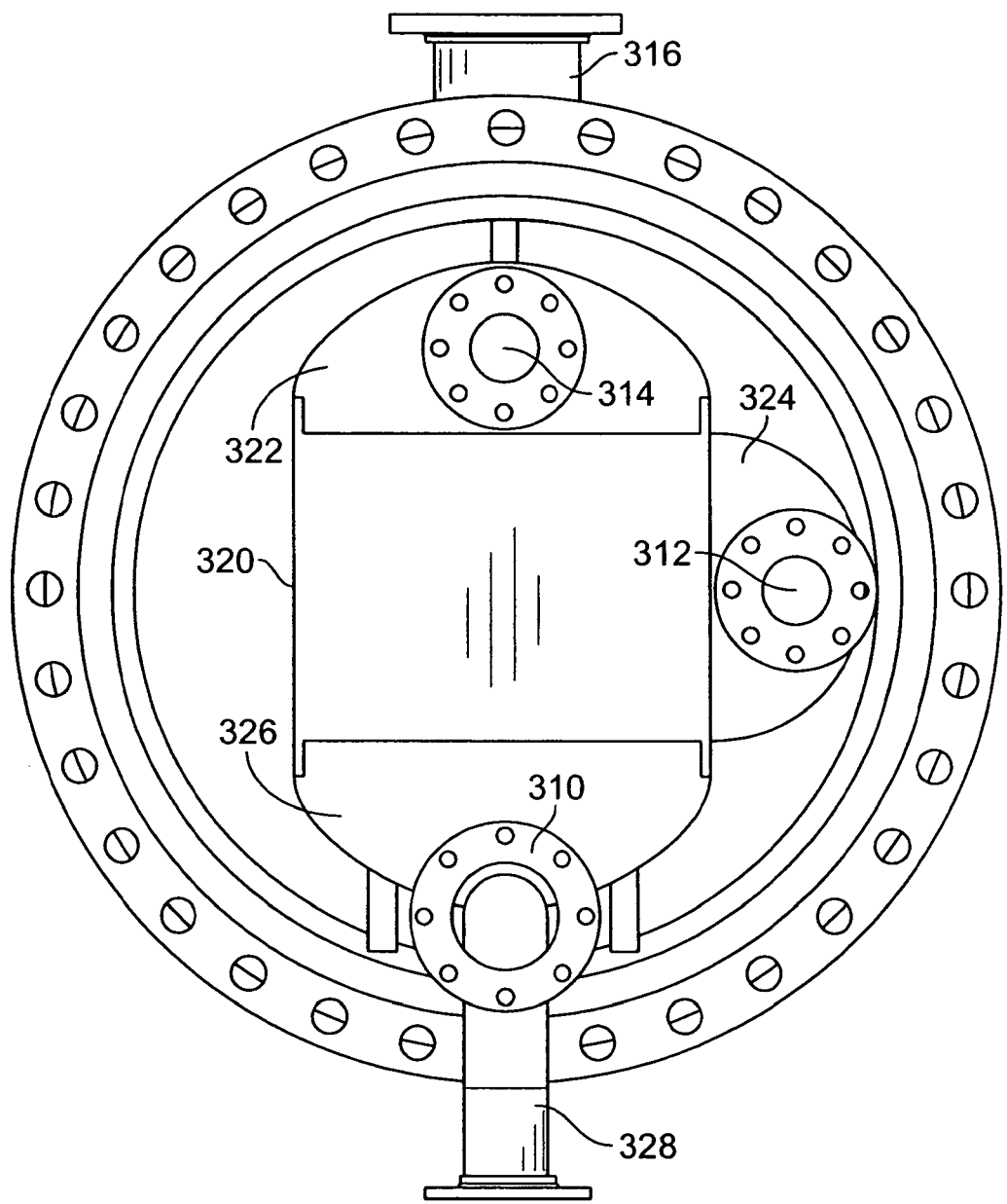
FIG. 18 is a frontal, cross-sectional view of the second exemplary embodiment of FIG. 14.
Figure 19:
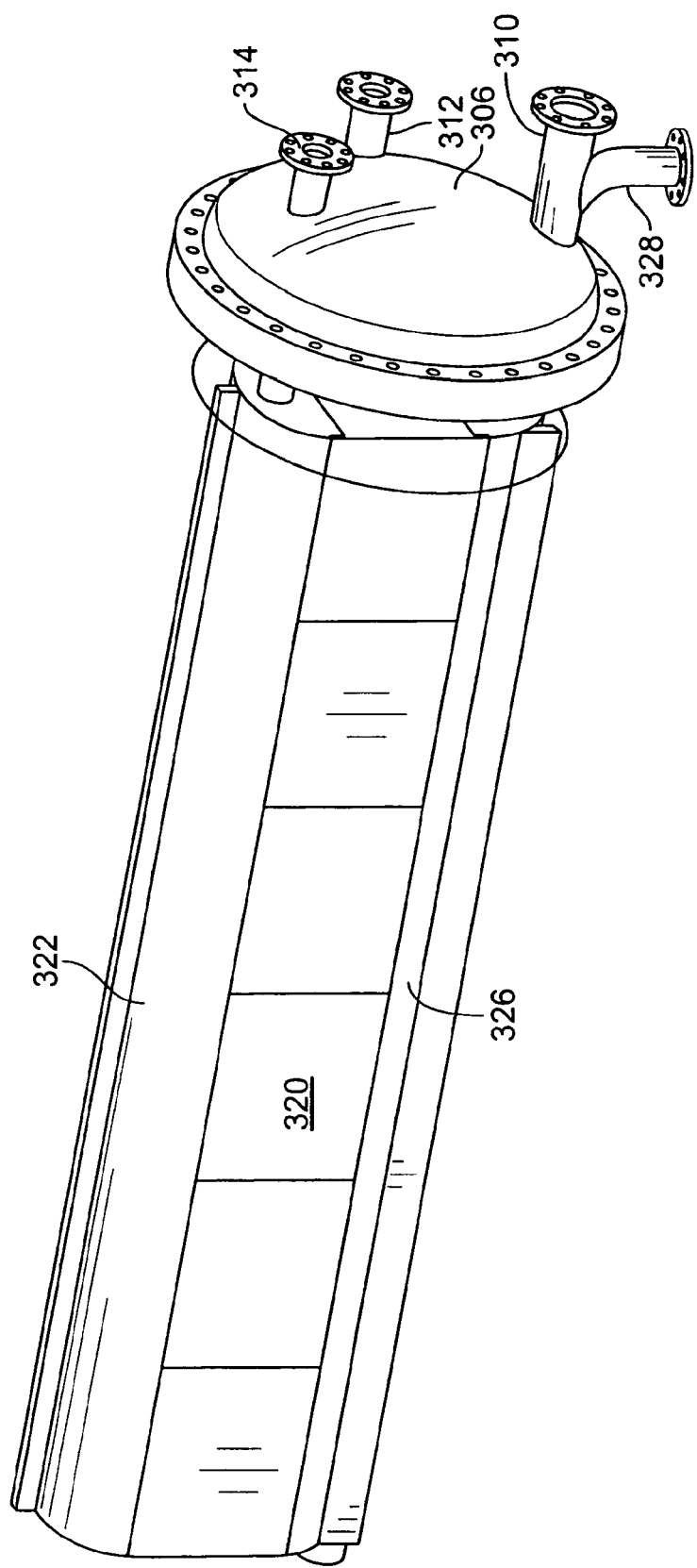
FIG. 19 is an elevated perspective view from the front of the second exemplary embodiment of FIG. 14, with the shell of the pressure vessel removed.
Figure 20:
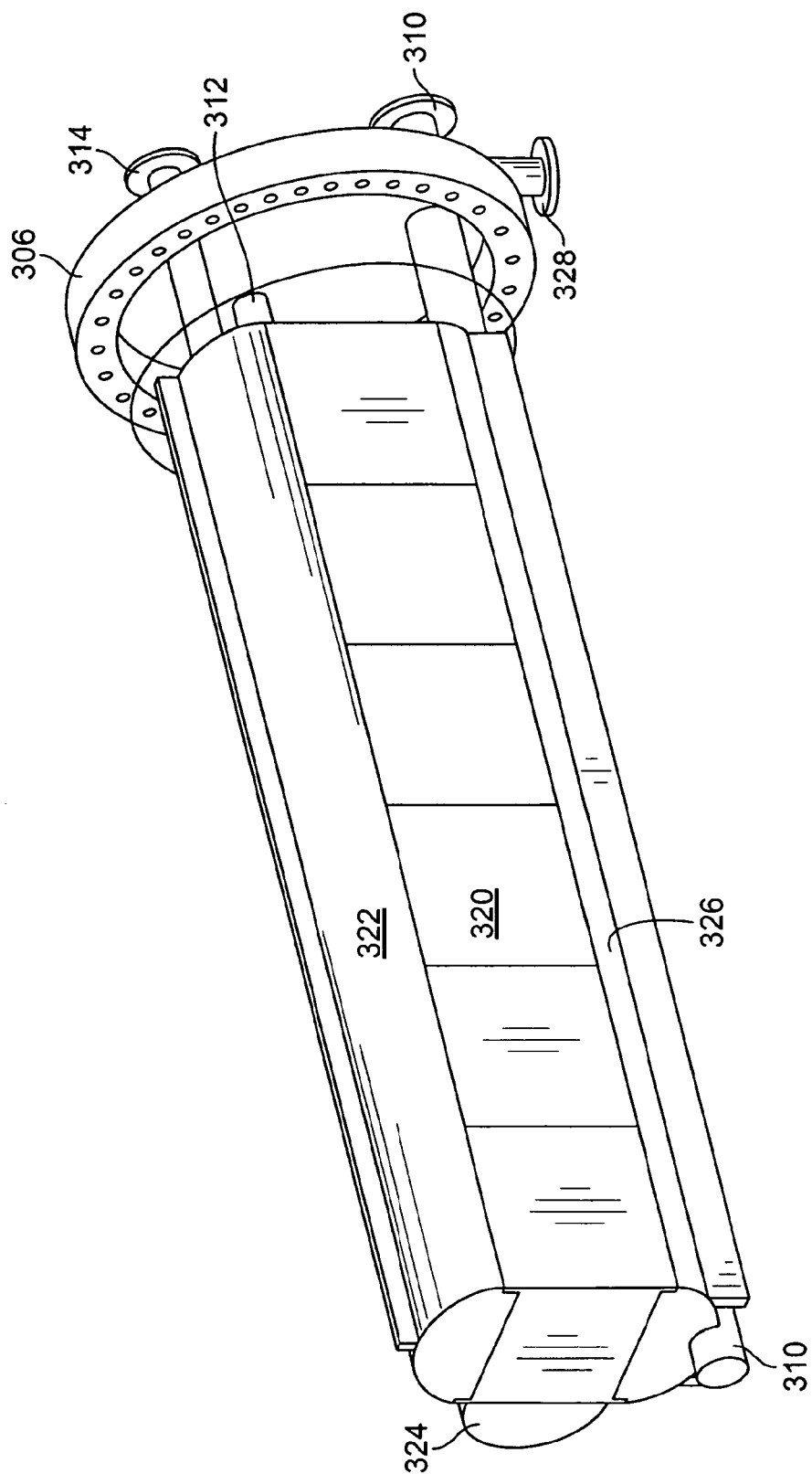
FIG. 20 is an elevated perspective view from the rear of the second exemplary embodiment of FIG. 14, with the shell of the pressure vessel removed.

Referencing FIG. 17, the present invention makes use of microchannel reactors 320 (FIG. 17) such as those disclosed in U.S. Pat. No. 6,192,596 entitled "Active microchannel fluid processing unit and method of making," and U.S. Pat. No. 6,622,519 entitled "Process for cooling a product in a heat exchanger employing microchannels for the flow of refrigerant and product," each of which is hereby incorporated by reference. Exemplary microchannel reactors 320 for use with the present invention are fabricated from stainless steel alloys and include interposed microchannels, where a first set of microchannels contain catalysts utilized for Fisher-Tropsch synthesis where the reactants (CO and $H_2$) form hydrocarbons and generate thermal energy, and a second set of microchannels carry a coolant adapted to remove at least a portion of the thermal energy generated by the Fisher-Tropsch synthesis.

Referring FIGS. 17-20, a series of microchannel reactors 320 are housed within the interior of the vessel 302 and receive a reactant stream with relatively high concentrations of carbon monoxide and hydrogen by way of the reactant conduit 314. A manifold 322 in communication with the reactant conduit 314 is welded to each of the reactors and operative to distribute the reactant stream amongst the six microchannel reactors 320. As the reactants flow through the microchannels (not shown), Fischer-Tropsch synthesis catalyst contained within the microchannels facilitates an exothermic reaction generating thermal energy. An internal coolant is delivered to the microchannel reactors 320 by way of the coolant conduit 312 feeding a manifold 324 welded to and distributing the coolant amongst the six microchannel reactors. In this exemplary embodiment, the coolant is boiler feed water entering the reactors 320 at approximately 220° C. and exiting the reactors as a mixture of liquid water and saturated steam opposite the manifold 324.

Superheated steam enters the reactors 320 by way of the steam conduit 310 in order to provide a flowing stream of product from the reactors 320. As discussed above, the products from the reactors 320 include high molecular weight hydrocarbons which may result in partial solidification within the microchannels. To inhibit the solid content of the products stream from blocking the microchannels, superheated steam is injected into the microchannels downstream from the reaction section of the microchannels to provide a source of thermal energy to the product stream and elevate the temperature within the product stream and ensure that fluid flow continues. As the product stream exits the reactors 320 via a welded manifold 326, the products are collected into a product conduit 328. The product conduit 328 is jacketed by the steam conduit 310 and provides a countercurrent heat exchanger providing more thermal energy (higher temperature steam) to the product stream as it travels farther downstream from the reactors 320.

The vessel 302 includes an active level control system (not shown) to inhibit the level of water within the vessel from reaching the outlets of the reactors 320 where water and steam are exiting. An orifice (not shown) within a lower circumferential area of the vessel 302 provides access to the water conduit 318 for removal of water from the vessel. It is envisioned that the water withdrawn from the vessel 302 be routed through the coolant conduit 312 to supply the boiler feed water. At the top of the vessel 302 is the steam outlet conduit 316 operative to withdraw the steam produced within the reactors 320. The active control system is also operative to maintain the fluid surrounding the reactors 320 at an elevated pressure so that the pressure exerted upon the exterior of the reactors is not significantly less than the pressures exerted upon the interior aspects of the reactors.

Those of ordinary skill will understand that the pressure exerted by the fluids surrounding the reactors 320 will vary depending upon the operating parameters chosen for the reactors. Nevertheless, it is within the scope of the present invention that the vessel be constructed to withstand internal pressures of 500 psig. Exemplary materials for use in fabricating the vessel 302 include, without limitation, SA 515, SA 516, and 1¼ chrome alloys.

Those of ordinary skill are familiar with commercially available catalysts for use in a Fisher-Tropsch synthesis. These catalysts include, without limitation, those disclosed and taught by U.S. patent application Ser. No. 10/766,297 entitled "Fischer-Tropsch Synthesis Using Microchannel Technology and Novel Catalyst and Microchannel Reactor," the disclosure of which is hereby incorporated by reference.

It is also within the scope of the present invention that the reactors 320 be removable from the manifolds 322, 324, 326. In this manner, the manifolds 322, 324, 326 are bolted to the reactors 320 with an interposing gasket to ensure a fluidic seal between the manifolds and reactors. Exemplary gaskets for use with this alternate exemplary embodiment include, without limitation, Garlock Helicoflex Spring Energized Seals, graphite gaskets, reinforced graphite, corrugated metal/spiral wound gaskets, and elastomeric seals. As discussed previously, welding of the reactors 320 introduces high local temperatures that may degrade or destroy catalyst in proximity to the weld and/or result in delaminations. In addition, the availability to quickly remove one or more reactors 320 from the vessel 302 obviates the need to provide separate catalyst refurbishment lines. In such an alternate exemplary embodiment, the refurbishment of active metal catalysts can occur away from the pressure vessel 304, as well as the ability to perform tests upon the reactors 320 away from the pressure vessel 304.

Following from the above description and invention summaries, it should be apparent to those of ordinary skill in the art that, while the methods and apparatuses herein described constitute exemplary embodiments of the present invention, the inventions contained herein are not limited to these precise embodiments and that changes may be made to them without departing from the scope of the invention as defined by the claims. Additionally, it is to be understood that the invention is defined by the claims and it is not intended that any limitations or elements describing the exemplary embodiments set forth herein are to be incorporated into the meanings of the claims unless such limitations or elements are explicitly recited in the claims. Likewise, it is to be understood that it is not necessary to meet any or all of the identified advantages or objects of the invention disclosed herein in order to fall within the scope of any claim, since the invention is defined by the claims and since inherent and/or unforeseen advantages of the present invention may exist even though they may not have been explicitly discussed herein.

What is claimed is:

1. A method of carrying out a Fischer-Tropsch synthesis comprising:

supporting a microchannel unit operation with an exterior support structure, the exterior support structure reinforcing an exterior of the microchannel unit operation, the microchannel unit operation including a first set of microchannels in fluid communication with a first inlet conduit and a first outlet conduit, and the microchannel unit operation including a second set of microchannels in thermal communication with the first set of microchannels, the second set of microchannels in fluid communication with a second inlet conduit and a second outlet conduit;

exerting a positive pressure upon the exterior of the microchannel unit operation by using a pressurized vessel as the exterior support structure, the pressurized vessel housing a fluid exerting the positive pressure upon the exterior of the microchannel unit operation;

directing a hydrogen source through the first inlet conduit;

directing carbon monoxide through the first inlet conduit;

reacting the carbon monoxide and the hydrogen source within the first set of microchannels to produce a hydrocarbon product;

heating a fluid stream flowing through the second set of microchannels from the reaction between the carbon monoxide and hydrogen source; and directing the hydrocarbon product through the first outlet conduit.

2. The method of claim 1, wherein:

the first inlet conduit and the first outlet conduit are fluidly coupled to the microchannel unit, operation proximate a first end of the microchannel unit operation; and the second inlet conduit and a second outlet conduit are fluidly coupled to the microchannel unit operation proximate the first end of the microchannel unit operation.

3. The method of claim 1, wherein the first set of microchannels house a Fischer Tropsch catalyst.

4. The method of claim 1, wherein:

the fluid stream flowing through the second set of microchannels comprises water; and the act of heating the fluid stream flowing through the second set of microchannels is operative to at least one of generate steam from liquid water and elevate the temperature of the water flowing through the second set of microchannels.

5. A method of carrying out a Fischer-Tropsch synthesis comprising:

supporting a microchannel unit operation with a pressure vessel, the pressure vessel exerting a positive pressure upon an exterior of the microchannel unit operation, the microchannel unit operation including a first set of microchannels in fluid communication with a first inlet conduit and a first outlet conduit, and the microchannel unit operation including a second set of microchannels in thermal communication with the first set of microchannels, the second set of microchannels in fluid communication with a second inlet conduit and a second outlet conduit;

directing a hydrogen source through the first inlet conduit;

directing carbon monoxide through the first inlet conduit;

reacting the carbon monoxide and the hydrogen source within the first set of microchannels to produce a hydrocarbon product;

heating a fluid stream flowing through the second set of microchannels from the reaction between the carbon monoxide and hydrogen source; and directing the hydrocarbon product through the first outlet conduit.

6. The method of claim 5, wherein:

the first inlet conduit and the first outlet conduit are fluidly coupled to the microchannel unit operation proximate a first end of the microchannel unit operation; and the second inlet conduit and a second outlet conduit are fluidly coupled to the microchannel unit operation proximate the first end of the microchannel unit operation.

7. The method of claim 5, wherein the first set of microchannels house a Fischer-Tropsch catalyst.

8. The method of claim 5, wherein:

the fluid stream flowing through the second set of microchannels comprises water; and the act of heating the fluid stream flowing through the second set of microchannels is operative to at least one of generate steam from liquid water and elevate the temperature of the water flowing through the second set of microchannels.

\* \* \* \* \*

UNITED STATES PATENT AND TRADEMARK OFFICE
CERTIFICATE OF CORRECTION

PATENT NO. : 8,450,381 B2
APPLICATION NO. : 13/427647
DATED : May 28, 2013
INVENTOR(S) : Rogers, Jr. et al.

It is certified that error appears in the above-identified patent and that said Letters Patent is hereby corrected as shown below:

On the Title Page, Item [75] "Inventors:" change the following inventor name from "Christopher Paul Well" to "Christopher Paul Weil"

Signed and Sealed this
Sixteenth Day of July, 2013

Teresa Stanek Rea
*Acting Director of the United States Patent and Trademark Office*